(12) United States Patent
Angibaud et al.

(10) Patent No.: US 7,511,138 B2
(45) Date of Patent: Mar. 31, 2009

(54) FARNESYL TRANSFERASE INHIBITING TRICYCLIC QUINAZOLINE DERIVATIVES SUBSTITUTED WITH CARBON-LINKED IMIDAZOLES OR TRIAZOLES

(75) Inventors: Patrick René Angibaud, Fontaine-Bellenger (FR); Marc Gaston Venet, Le Mesnil Esnard (FR); Jean Michel Jacques Raymond Argoullon, Bihorel (FR)

(73) Assignee: Janssen Pharmaceutica NV, Beerse (BE)

( * ) Notice: Subject to any disclaimer, the term of this patent is extended or adjusted under 35 U.S.C. 154(b) by 460 days.

(21) Appl. No.: 10/509,365

(22) PCT Filed: Apr. 14, 2003

(86) PCT No.: PCT/EP03/03986

§ 371 (c)(1), (2), (4) Date: Sep. 24, 2004

(87) PCT Pub. No.: WO03/087101

PCT Pub. Date: Oct. 23, 2003

(65) Prior Publication Data

US 2005/0148609 A1      Jul. 7, 2005

(30) Foreign Application Priority Data

Apr. 15, 2002    (EP) ................... 02076448

(51) Int. Cl.
C07D 471/00 (2006.01)
C07D 487/00 (2006.01)
A01N 43/58 (2006.01)
A61K 31/50 (2006.01)

(52) U.S. Cl. ..................... 544/251; 544/249
(58) Field of Classification Search ............... 544/249, 544/251; 514/248
See application file for complete search history.

(56) References Cited

U.S. PATENT DOCUMENTS

| 6,187,786 B1 | 2/2001 | Venet et al. |
| 2002/0049327 A1 | 4/2002 | Venet et al. |

FOREIGN PATENT DOCUMENTS

| EP | 0371564 A2 | 6/1990 |
| EP | 0371564 B1 | 6/1990 |
| WO | WO 97/16443 A1 | 5/1997 |
| WO | WO 97/21701 A1 | 6/1997 |
| WO | WO 98/40383 A1 | 9/1998 |
| WO | WO 98/49157 A1 | 11/1998 |
| WO | WO 98/55124 A1 | 12/1998 |
| WO | WO 00/01386 A1 | 1/2000 |
| WO | WO 00/01411 A1 | 1/2000 |
| WO | WO 00/12498 A1 | 3/2000 |
| WO | WO 00/12499 A1 | 3/2000 |
| WO | WO 00/39082 A2 | 7/2000 |
| WO | WO 00/47574 A1 | 8/2000 |
| WO | WO 01/53289 A1 | 7/2001 |
| WO | WO 01/98302 A1 | 12/2001 |
| WO | WO 02/24637 A1 | 3/2002 |
| WO | WO 02/24682 A2 | 3/2002 |
| WO | WO 02/24683 A1 | 3/2002 |
| WO | WO 02/24686 A2 | 3/2002 |

OTHER PUBLICATIONS

Kohl, et al., "Selective Inhibition of ras-Dependent Transformation by a Farnesyltransferase Inhibitor", Science, 1993, vol. 260, 1934-1937.
Oertel, F., "Zur Synthese von '1, 2, 3, 4!tetrazolo'1, 5-a!-und 1, 5-b!chinazolinen" Pharmazie, 1990, vol. 45 No. 5, p. 370.
Rak, J., et al., "Mutant ras Oncogenes Upregulate VEGF/VPF Expression: Implications for Induction and Inhibition of Tumor Angiogenses¹", Cancer Research, 1995, 55(20), 4575-80.
International Search Report mailed Aug. 5, 2003 for PCT/EP 03/03986.

*Primary Examiner*—James O. Wilson
*Assistant Examiner*—Paul V. Ward

(57) ABSTRACT

This invention comprises the novel compounds of formula (I) wherein r, s, t, $R^1$, $R^2$, $R^3$, $R^4$, $R^5$, and $R^6$ have defined meanings, having farnesyl transferase inhibiting activity; their preparation, compositions containing them and their use as a medicine.

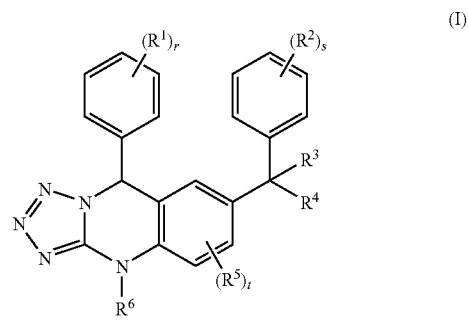

7 Claims, No Drawings

FARNESYL TRANSFERASE INHIBITING TRICYCLIC QUINAZOLINE DERIVATIVES SUBSTITUTED WITH CARBON-LINKED IMIDAZOLES OR TRIAZOLES

CROSS REFERENCE TO RELATED APPLICATIONS

This application is a National Stage application under 35 U.S.C. § 371 of International Application No. PCT/EP03/03986 filed 14 Apr. 2003, which claims priority from EP02076448.6, filed 15 Apr. 2002, the contents of which are hereby incorporated by reference.

The present invention is concerned with novel tricyclic quinazoline derivatives substituted with carbon-linked imidazoles or triazoles, the preparation thereof, pharmaceutical compositions comprising said novel compounds and the use of these compounds as a medicine as well as methods of treatment by administering said compounds.

Oncogenes frequently encode protein components of signal transduction pathways which lead to stimulation of cell growth and mitogenesis. Oncogene expression in cultured cells leads to cellular transformation, characterized by the ability of cells to grow in soft agar and the growth of cells as dense foci lacking the contact inhibition exhibited by non-transformed cells. Mutation and/or overexpression of certain oncogenes is frequently associated with human cancer. A particular group of oncogenes is known as ras which have been identified in mammals, birds, insects, mollusks, plants, fungi and yeasts. The family of mammalian ras oncogenes consists of three major members ("isoforms"): H-ras, K-ras and N-ras oncogenes. These ras oncogenes code for highly related proteins generally known as $p21^{ras}$. Once attached to plasma membranes, the mutant or oncogenic forms of $p21^{ras}$ will provide a signal for the transformation and uncontrolled growth of malignant tumor cells. To acquire this transforming potential, the precursor of the $p21^{ras}$ oncoprotein must undergo an enzymatically catalyzed farnesylation of the cysteine residue located in a carboxyl-terminal tetrapeptide. Therefore, inhibitors of the enzymes that catalyzes this modification, i.e. farnesyl transferase, will prevent the membrane attachment of $p21^{ras}$ and block the aberrant growth of ras-transformed tumors. Hence, it is generally accepted in the art that farnesyl transferase inhibitors can be very useful as anticancer agents for tumors in which ras contributes to transformation.

Since mutated oncogenic forms of ras are frequently found in many human cancers, most notably in more than 50% of colon and pancreatic carcinomas (Kohl et al., *Science*, vol 260, 1834-1837, 1993), it has been suggested that farnesyl tranferase inhibitors can be very useful against these types of cancer.

In EP-0,371,564 there are described (1H-azol-1-ylmethyl) substituted quinoline and quinolinone derivatives which suppress the plasma elimination of retinoic acids. Some of these compounds also have the ability to inhibit the formation of androgens from progestines and/or inhibit the action of the aromatase enzyme complex.

In WO 97/16443, WO 97/21701, WO 98/40383 and WO 98/49157, there are described 2-quinolone derivatives which exhibit farnesyl transferase inhibiting activity. WO 00/39082 describes a class of novel 1,2-annelated quinoline compounds, bearing a nitrogen- or carbon-linked imidazole, which show farnesyl protein transferase and geranylgeranyl transferase inhibiting activity. Other quinolinone and quinazolne compounds having farnesyl transferase inhibiting activity are described in WO 00/12498, WO 00/12499, WO 00/47574, WO 01/53289, WO 01/98302, WO 02/24682, WO 02/24683, WO 02/24686 and WO 02/24687.

Unexpectedly, it has been found that the present novel compounds, all having a phenyl substituent on the 4-position of the 2,3-annelated quinolinone moiety bearing a carbon-linked imidazole or triazole, show farnesyl protein transferase inhibiting activity. The present compounds can have advantageous properties with regard to solubility and stability.

The present invention concerns compounds of formula (I):

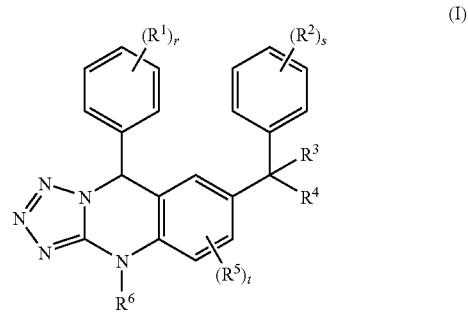

or a pharmaceutically acceptable salt or N-oxide or stereochemically isomeric form thereof, wherein
r and s are each independently 0, 1, 2 or 3;
t is 0, 1, or 2;
each $R^1$ and $R^2$ are independently hydroxy, halo, cyano, nitro, $C_{1-6}$alkyl, $-(CR^{16}R^{17})_p$, $-C_{3-10}$cycloalkyl, cyano$C_{1-6}$alkyl, hydroxy$C_{1-6}$alkyl, $C_{1-6}$alkyloxy$C_{1-6}$alkyl, hydroxycarbonyl$C_{1-6}$alkyl, $R^{20}SC_{1-6}$alkyl, trihalomethyl, aryl$C_{1-6}$alkyl, Het$^1C_{1-6}$alkyl, $-C_{1-6}$alkyl-$NR^{18}R^{19}$, $-C_{1-6}$alkyl$NR^{18}C_{1-6}$alkyl-$NR^{18}R^{19}$, $-C_{1-6}$alkyl$NR^{18}COC_{1-6}$alkyl, $-C_{1-6}$alkyl$NR^{18}$COAlkAr$^1$, $-C_{1-6}$alkyl$NR^{18}$COAr$^1$, $C_{1-6}$alkylsulphonylamino$C_{1-6}$alkyl, $C_{1-6}$alkyloxy, hydroxy$C_{1-6}$alkyloxy, $C_{1-6}$alkyloxy$C_{1-6}$alkyloxy, $-OC_{1-6}$alkyl-$NR^{18}R^{19}$, trihalomethoxy, aryl$C_{1-6}$alkyloxy, Het$^1C_{1-6}$alkyloxy, $C_{2-6}$alkenyl, cyano$C_{2-6}$alkenyl, $-C_{2-6}$alkenyl-$NR^{18}R^{19}$, hydroxycarbonyl$C_{2-6}$alkenyl, $C_{1-6}$alkyloxycarbonyl$C_{2-6}$alkenyl, $C_{2-6}$alkynyl, $-CHO$, $C_{1-6}$alkylcarbonyl, hydroxy$C_{1-6}$alkylcarbonyl, hydroxycarbonyl, $C_{1-6}$alkyloxycarbonyl, $-CONR^{18}R^{19}$, $-CONR^{18}-C_{1-6}$alkyl-$NR^{18}R^{19}$, $-CONR^{18}-C_{1-6}$ alkyl-Het$^1$, $-CONR^{18}-C_{1-6}$alkyl-Ar$^1$, $-CONR^{18}-O-C_{1-6}$alkyl, $-CONR^{18}-C_{1-6}$alkenyl, $-NR^{18}R^{19}$, $-OC(O)R^{20}$, $-CR^{20}=NR^{21}$, $-CR^{20}=N-OR^{21}$, $-NR^{20}C(O)NR^{18}R^{19}$, $-NR^{20}SO_2R^{21}$, $-NR^{20}C(O)R^{21}$, $-S-R^{20}$, $-S(O)-R^{20}$, $-S(O)_2R^{20}$, $-SO_2NR^{20}R^{21}$, $-C(NR^{22}R^{23})=NR^{24}$,
or a group of formula
    $-CO-Z$ or $-CO-NR^y-Z$ in which $R^y$ is hydrogen or $C_{1-4}$alkyl and Z is phenyl or a 5- or 6-membered heterocyclic ring containing one or more heteroatoms selected from oxygen, sulphur and nitrogen, the phenyl or heterocyclic ring being optionally substituted by one or two substituents each independently selected from halo, cyano, hydroxycarbonyl, aminocarbonyl, $C_{1-6}$alkylthio, hydroxy, $-NR^{18}R^{19}$, $C_{1-6}$alkylsulphonylamino, $C_{1-6}$alkyl, halo$C_{1-6}$alkyl, $C_{1-6}$alkyloxy or phenyl; or
two $R^1$ and $R^2$ substituents adjacent to one another on the phenyl ring may independently form together a bivalent radical of formula —O—CH$_2$—O— (a-1)

—O—CH$_2$—CH$_2$—O— (a-2)

—O—CH═CH— (a-3)

—O—CH$_2$—CH$_2$— (a-4) or

—O—CH$_2$—CH$_2$—CH$_2$— (a-5)

$R^{16}$ and $R^{17}$ are independently hydrogen or $C_{1-6}$ alkyl;

$R^{18}$ and $R^{19}$ are independently hydrogen, $C_{1-6}$ alkyl or —(CR$^{16}$R$^{17}$)$_p$—$C_{3-10}$cycloalkyl, or together with the adjacent nitrogen atom form a 5- or 6-membered heterocyclic ring optionally containing one, two or three further heteroatoms selected from oxygen, nitrogen or sulphur and optionally substituted by one or two substituents each independently selected from halo, hydroxy, cyano, nitro, $C_{1-6}$alkyl, halo$C_{1-6}$alkyl, $C_{1-6}$alkyloxy, OCF$_3$, hydroxycarbonyl, $C_{1-6}$alkyloxycarbonyl, aminocarbonyl, mono- or di-($C_{1-6}$alkyl)aminocarbonyl, amino, mono- or di($C_{1-6}$alkyl)amino, $C_{1-6}$alkylsulfonylamino, oxime, or phenyl;

$R^{20}$ and $R^{21}$ are independently hydrogen, $C_{1-6}$alkyl, —CR$^{16}$R$^{17}$)$_p$—$C_{3-10}$cycloalkyl or aryl$C_{1-6}$alkyl;

$R^{22}$, $R^{23}$ and $R^{24}$ are independently hydrogen and $C_{1-6}$alkyl or C(O)$C_{1-6}$alkyl;

p is 0 or 1;

$R^3$ is hydrogen, halo, cyano, $C_{1-6}$alkyl, —(CR$^{16}$R$^{17}$)$_p$—$C_{3-10}$ cycloalkyl, halo$C_{1-6}$alkyl, cyano$C_{1-6}$alkyl, hydroxy$C_{1-6}$ alkyl, $C_{1-6}$alkyloxy$C_{1-6}$alkyl, aryl$C_{1-6}$alkyloxy $C_{1-6}$alkyl, $C_{1-6}$alkylthio$C_{1-6}$alkyl, hydroxycarbonyl$C_{1-6}$alkyl, $C_{1-6}$alkylcarbonyl $C_{1-6}$alkyl, $C_{1-6}$alkyloxycarbonyl$C_{1-6}$alkyl, —$C_{1-6}$alkyl-NR$^{18}$R$^{19}$, —$C_{1-6}$alkyl-CONR$^{18}$R$^{19}$, aryl$C_{1-6}$alkyl, Het$^1$$C_{1-6}$alkyl, $C_{2-6}$alkenyl, —$C_{2-6}$alkenyl NR$^{18}$R$^{19}$, $C_{2-6}$alkynyl, hydroxycarbonyl, $C_{1-6}$alkyloxycarbonyl, aryl, or Het$^1$; or a radical of formula —O—R$^7$ (b-1)

—S—R$^7$ (b-2)

—NR$^8$R$^9$ (b-3) or

—N═CR$^7$R$^8$ (b-4)

wherein R$^7$ is hydrogen, $C_{1-6}$alkyl, —(CR$^{16}$R$^{17}$)$_p$—$C_{3-10}$cycloalkyl, aryl$C_{1-6}$alkyl, $C_{2-6}$alkenyl, $C_{2-6}$alkynyl, $C_{1-6}$alkylcarbonyl or —$C_{1-6}$alkylC(O)O$C_{1-6}$alkyl NR$^{18}$R$^{19}$, or a radical of formula -Alk-OR$^{10}$ or -Alk-NR$^{11}$R$^{12}$;

R$^8$ is hydrogen, $C_{1-6}$alkyl, —(CR$^{16}$R$^{17}$)$_p$—$C_{3-10}$cycloalkyl, $C_{2-6}$alkenyl or $C_{2-6}$alkynyl;

R$^9$ is hydrogen, hydroxy, $C_{1-6}$alkyl, —(CR$^{16}$R$^{17}$)$_p$—$C_{3-10}$ cycloalkyl, $C_{1-6}$alkylcarbonyl$C_{1-6}$alkyl, aryl$C_{1-6}$alkyl, $C_{2-6}$alkenyl, $C_{2-6}$alkynyl, aryl, $C_{1-6}$alkyloxy, a group of formula —NR$^{18}$R$^{19}$, $C_{1-6}$alkylcarbonylamino, $C_{1-6}$alkylcarbonyl, halo$C_{1-6}$alkylcarbonyl, aryl$C_{1-6}$alkylcarbonyl, arylcarbonyl, $C_{1-6}$alkyloxycarbonyl, trihalo$C_{1-6}$alkyloxycarbonyl, $C_{1-6}$alkyloxy$C_{1-4}$alkylcarbonyl, aminocarbonyl, mono- or di($C_{1-6}$alkyl)aminocarbonyl wherein the alkyl moiety may optionally be substituted by one or more substituents independently selected from aryl and $C_{1-6}$alkyloxycarbonyl substituents; aminocarbonylcarbonyl, mono- or di($C_{1-6}$alkyl)amino$C_{1-6}$alkylcarbonyl, or a radical of formula -Alk-OR$^{10}$ or Alk-NR$^{11}$R$^{12}$;

wherein Alk is $C_{1-6}$alkanediyl;

R$^{10}$ is hydrogen, $C_{1-6}$alkyl, —(CR$^{16}$R$^{17}$)$_p$—$C_{3-10}$cycloalkyl, $C_{2-6}$alkenyl, $C_{2-6}$alkynyl, $C_{1-6}$alkylcarbonyl or hydroxy$C_{1-6}$alkyl;

R$^{11}$ is hydrogen, $C_{1-6}$alkyl, —(CR$^{16}$R$^{17}$)$_p$—$C_{3-10}$cycloalkyl, $C_{2-6}$alkenyl or $C_{2-6}$alkynyl;

R$^{12}$ is hydrogen, $C_{1-6}$alkyl, —(CR$^{16}$R$^{17}$)$_p$—$C_{3-10}$cycloalkyl, $C_{2-6}$alkenyl, $C_{2-6}$alkynyl or $C_1$-alkylcarbonyl;

R$^4$ is a radical of formula

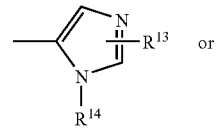
(c-1)

or

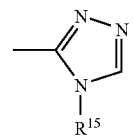
(c-2)

wherein R$^{13}$ is hydrogen, halo or $C_{1-6}$alkyl;

R$^{14}$ is hydrogen or $C_{1-6}$alkyl;

R$^{15}$ is hydrogen or $C_{1-6}$alkyl;

R$^5$ is cyano, hydroxy, halo, $C_{1-6}$alkyl, —(CR$^{16}$R$^{17}$)$_p$—$C_{3-10}$cycloalkyl, $C_{2-6}$alkenyl, $C_{2-6}$alkynyl, $C_{1-6}$alkyloxy, hydroxycarbonyl, $C_{1-6}$alkyloxycarbonyl, or a group of formula —NR$^{18}$R$^{19}$ or —CONR$^{18}$R$^{19}$;

R$^6$ is hydrogen, $C_{1-6}$alkyl, —(CR$^{16}$R$^{17}$)$_p$—$C_{3-10}$cycloalkyl, cyano$C_{1-6}$alkyl, —$C_{1-6}$alkylCO$_2$R$^{20}$, aminocarbonyl$C_{1-6}$ alkyl, —$C_{1-6}$alkyl-NR$^{18}$R$^{19}$, R$^{20}$SO$_2$, R$^{20}$SO$_2$$C_{1-6}$alkyl, —$C_{1-6}$alkyl-OR$^{20}$, —$C_{1-6}$alkyl-SR$^{20}$, —$C_{1-6}$alkyl-CONR$^{18}$—$C_{1-6}$alkyl-NR$^{18}$R$^{19}$, —$C_{1-6}$alkylCONR$^{18}$—$C_{1-6}$alkyl-Het$^1$, —$C_{1-6}$alkylCONR$^{18}$—$C_{1-6}$alkyl-Ar$^1$, —$C_{1-6}$alkylCONR$^{18}$-Het$^1$, —$C_{1-6}$-alkylCONR$^{18}$Ar$^1$, —$C_{1-6}$alkylCONR$^{18}$—O—$C_{1-6}$alkyl, —$C_{1-6}$alkyl-CONR$^{18}$—$C_{1-6}$alkenyl, -Alk-Ar$^1$ or -AlkHet$^1$;

Ar$^1$ is phenyl, naphthyl or phenyl or naphthyl substituted by one to five substituents each independently selected from halo, hydroxy, cyano, nitro, $C_{1-6}$alkyl, halo$C_{1-6}$alkyl, -alkylNR$^{18}$R$^{19}$, $C_{1-6}$alkyloxy, OCF$_3$, hydroxycarbonyl, $C_{1-6}$alkyloxycarbonyl, —CONR$^{18}$R$^{19}$, —NR$^{18}$R$^{19}$, $C_{1-6}$alkylsulfonylamino, oxime, phenyl, or a bivalent substituent of formula —O—CH$_2$—O— or

—O—CH$_2$—CH$_2$—O—;

Het$^1$ is a mono- or bi-cyclic heterocyclic ring containing one or more heteroatoms selected from oxygen, sulphur and nitrogen and optionally substituted by one or two substituents each independently selected from halo, hydroxy, cyano, nitro, $C_{1-6}$alkyl, halo$C_{1-6}$alkyl, -alkylNR$^{18}$R$^{19}$, $C_{1-6}$alkyloxy, OCF$_3$, hydroxycarbonyl, $C_{1-6}$alkyloxycarbonyl, —CONR$^{18}$R$^{19}$, —NR$^{18}$R$^{19}$, $C_{1-6}$alkylsulfonylamino, oxime or phenyl.

As used in the foregoing definitions and hereinafter, halo is generic to fluoro, chloro, bromo and iodo; $C_{1-4}$alkyl defines straight and branched chain saturated hydrocarbon radicals having from 1 to 4 carbon atoms such as, e.g. methyl, ethyl, propyl, butyl, 1-methylethyl, 2-methylpropyl and the like; $C_{1-6}$alkyl includes $C_{1-4}$alkyl and the higher homologues thereof having 5 to 6 carbon atoms such as, for example, pentyl, 2-methyl-butyl, hexyl, 2-methylpentyl and the like; $C_{1-6}$alkanediyl defines bivalent straight and branched chained saturated hydrocarbon radicals having from 1 to 6 carbon atoms, such as, for example, methylene, 1,2-ethanediyl, 1,3-propanediyl, 1,4-butanediyl, 1,5-pentanediyl, 1,6-hexanediyl and the branched isomers thereof; halo$C_{1-6}$alkyl defines $C_{1-6}$alkyl containing one or more halo substituents for example trifluoromethyl; $C_{2-6}$alkenyl defines straight and branched chain hydrocarbon radicals containing one double bond and having from 2 to 6 carbon atoms such as, for example, ethenyl, 2-propenyl, 3-butenyl, 2-pentenyl, 3-pentenyl, 3-methyl-2-butenyl, and the like; $C_{2-6}$alkynyl defines straight and branched chain hydrocarbon radicals containing one triple bond and having from 2 to 6 carbon atoms such as, for example, ethynyl, 2-propynyl, 3-butynyl, 2-pentynyl, 3-pentynyl, 3-methyl-2-butynyl, and the like; the term "S(O)" refers to a sulfoxide and "S(O)$_2$" to a sulfone; aryl defines phenyl, naphthalenyl, phenyl substituted with one or more substituents each independently selected from halo, $C_{1-6}$alkyl, $C_{1-6}$alkyloxy, trifluoromethyl, cyano, or hydroxycarbonyl; or naphtalenyl substituted with one or more substituents each independently selected from halo, $C_{1-6}$alkyl, $C_{1-6}$alkyloxy, trifluoromethyl, cyano or hydroxycarbonyl; $C_{3-10}$cycloalkyl includes cyclic hydrocarbon groups having from 3 to 10 carbons, such as cyclopropyl, cyclobutyl, cyclopentyl, cyclopentenyl, cyclohexyl, cyclohexenyl, cycloheptyl, cyclooctyl and the like.

Pharmaceutically acceptable addition salts encompass pharmaceutically acceptable acid addition salts and pharmaceutically acceptable base addition salts. The pharmaceutically acceptable acid addition salts as mentioned hereinabove are meant to comprise the therapeutically active non-toxic acid addition salt forms which the compounds of formula (I) are able to form. The compounds of formula (I) which have basic properties can be converted in their pharmaceutically acceptable acid addition salts by treating said base form with an appropriate acid. Appropriate acids comprise, for example, inorganic acids such as hydrohalic acids, e.g. hydrochloric or hydrobromic acid; sulfuric; nitric; phosphoric and the like acids; or organic acids such as, for example, acetic, propanoic, hydroxyacetic, lactic, pyruvic, oxalic, malonic, succinic (i.e. butanedioic acid), maleic, fumaric, malic, tartaric, citric, methanesulfonic, ethanesulfonic, benzenesulfonic, p-toluenesulfonic, cyclamic, salicylic, p-amino-salicylic, pamoic and the like acids.

The compounds of formula (I) which have acidic properties may be converted in their pharmaceutically acceptable base addition salts by treating said acid form with a suitable organic or inorganic base. Appropriate base salt forms comprise, for example, the ammonium salts, the alkali and earth alkaline metal salts, e.g. the lithium, sodium, potassium, magnesium, calcium salts and the like, salts with organic bases, e.g. the benzathine, N-methyl-D-glucamine, hydrabamine salts, and salts with amino acids such as, for example, arginine, lysine and the like.

The term "acid or base addition salts" also comprises the hydrates and the solvent addition forms which the compounds of formula (I) are able to form. Examples of such forms are e.g. hydrates, alcoholates and the like.

The term stereochemically isomeric forms of compounds of formula (I), as used hereinbefore, defines all possible compounds made up of the same atoms bonded by the same sequence of bonds but having different three-dimensional structures which are not interchangeable, which the compounds of formula (I) may possess. Unless otherwise mentioned or indicated, the chemical designation of a compound encompasses the mixture of all possible stereochemically isomeric forms which said compound may possess. Said mixture may contain all diastereomers and/or enantiomers of the basic molecular structure of said compound. All stereochemically isomeric forms of the compounds of formula (I) both in pure form or in admixture with each other are intended to be embraced within the scope of the present invention.

Some of the compounds of formula (I) may also exist in their tautomeric forms. Such forms although not explicitly indicated in the above formula are intended to be included within the scope of the present invention.

Whenever used hereinafter, the term "compounds of formula (I)" is meant to include also the pharmaceutically acceptable acid addition salts and all stereoisomeric forms.

A group of interesting compounds consists of those compounds of formula (I) wherein one or more of the following restrictions apply:

a) r and s are each independently 0, 1 or 2;
b) t is 0 or 1;
c) $R^1$ is halo, $C_{1-6}$alkyl, $-(CR^{16}R^{17})_p-C_{3-10}$cycloalkyl, trihalomethyl, cyano, trihalomethoxy, $C_{2-6}$alkenyl, hydroxycarbonyl$C_{2-6}$alkenyl, $C_{2-6}$alkynyl, $C_{1-6}$alkyloxy, hydroxy$C_{1-6}$alkyloxy, amino$C_{1-6}$alkyloxy, hydroxycarbonyl, $C_{1-6}$alkyloxycarbonyl, $-CONR^{18}R^{19}$, or $-CH=NOR^{21}$; or two $R^1$ substituents adjacent to one another on the phenyl ring may independently form together a bivalent radical of formula $-O-CH_2-O-$ (a-1), or $-O-CH_2-CH_2-O-$ (a-2);

d) $R^2$ is halo, cyano, nitro, cyano$C_{1-6}$alkyl, hydroxy$C_{1-6}$alkyl, $-C_{1-6}$alkyl $NR^{18}R^{19}$, $Het^1C_{1-6}$alkyl, cyano$C_{2-6}$alkenyl, $-NR^{18}R^{19}$, CHO, hydroxycarbonyl, $C_{1-6}$alkyloxycarbonyl, $-CO NR^{18}R^{19}$; or two $R^2$ substituents adjacent to one another on the phenyl ring may independently form together a bivalent radical of formula $-O-CH_2-O-$ (a-1), or $-O-CH_2-CH_2-O-$ (a-2);

e) $R^3$ is hydrogen, halo, $C_{1-6}$alkyl, $-(CR^{16}R^{17})_p-C_{3-10}$cycloalkyl, halo$C_{1-6}$alkyl, cyano$C_1$-alkyl, hydroxy$C_{1-6}$alkyl, $C_{1-6}$alkyloxy$C_{1-6}$alkyl, $-C_{1-6}$alkyl $NR^{18}R^{19}$, $Het^1C_{1-6}$alkyl, $-C_{2-6}$alkenyl $NR^{18}R^{19}$, or -$Het^1$; or a group of formula $-O-R^7$ (b-1), or $-NR^8R^9$ (b-3), wherein $R^7$ is hydrogen, $C_{1-6}$alkyl, or $-(CR^{16}R^{17})_p-C_{3-10}$cycloalkyl, or a group of formula -Alk-OR$^{10}$ or -Alk-NR$^{11}R^{12}$;

$R^8$ is hydrogen or $C_{1-6}$alkyl;

$R^9$ is hydrogen, hydroxy, $C_{1-6}$alkyl, $-(CR^{16}R^{17})_p-C_{3-10}$cycloalkyl, $C_{1-6}$alkyloxy, $C_{1-6}$alkylcarbonyl, aminocarbonyl, or a radical of formula -Alk-OR$^{10}$ or Alk-NR$^{11}R^{12}$;

wherein Alk is $C_{1-6}$alkanediyl;

$R^{10}$ is hydrogen, $C_{1-6}$alkyl or $-(CR^{16}R^{17})_p-C_{3-10}$cycloalkyl;

$R^{11}$ is hydrogen, $C_{1-6}$alkyl, or $-(CR^{16}R^{17})_p-C_{3-10}$cycloalkyl;

$R^{12}$ is hydrogen or $C_{1-6}$alkyl;

f) $R^4$ is a radical of formula (c-1) or (c-2) wherein
   $R^{13}$ is hydrogen;
   $R^{14}$ is $C_{1-6}$alkyl;
   $R^{15}$ is $C_{1-6}$alkyl;
g) $R^6$ is hydrogen, $C_{1-6}$alkyl, —$C_{1-6}$alkylCO$_2$R$^{20}$, —$C_{1-6}$alkyl-C(O)NR$^{18}$R$^{19}$, -Alk-Ar$^1$, -AlkHet$^1$ or —(CR$^{16}$R$^{17}$)$_p$—$C_{3-10}$cycloalkyl,
h) Het$^1$ is a 5- or 6-membered monocyclic heterocyclic ring containing one, two or three heteroatoms selected from oxygen, sulphur or nitrogen for example pyrrolidinyl, imidazolyl, triazolyl, pyridyl, pyrimidinyl, furyl, morpholinyl, piperazinyl, piperidinyl, thiophenyl, thiazolyl or oxazolyl, or a 9- or 10-membered bicyclic heterocyclic ring especially one in which a benzene ring is fused to a heterocyclic ring containing one, two or three heteroatoms selected from oxygen, sulphur or nitrogen for example indolyl, quinolinyl, benzimidazolyl, benzotriazolyl, benzoxazolyl, benzothiazolyl or benzodioxolanyl.

Another group of interesting compounds consists of those compounds of formula (I) wherein one or more of the following restrictions apply:
a) r is 0, 1 or 2;
b) s is 0 or 1;
c) t is 0;
d) $R^1$ is halo, cyano, $C_{1-6}$alkyl or two $R^1$ substituents ortho to one another on the phenyl ring may independently form together a bivalent radical of formula (a-1);
e) $R^2$ is halo, cyano, cyano$C_{1-6}$alkyl, hydroxy$C_{1-6}$alkyl, —$C_{1-6}$ alkyl NR$^{18}$R$^{19}$, Het$^1$C$_{1-6}$alkyl, CHO, oxime, hydroxycarbonyl, or two $R^2$ substituents ortho to one another on the phenyl ring may independently form together a bivalent radical of formula (a-1);
f) $R^3$ is hydrogen, Het$^1$ or a group of formula (b-1) or (b-3) wherein
   $R^7$ is hydrogen or a group of formula -Alk-OR$^{10}$.
   $R^8$ is hydrogen;
   $R^9$ is hydrogen, $C_{1-6}$alkyl, $C_{1-6}$alkylcarbonyl, hydroxy, $C_{1-6}$alkyloxy or mono- or di($C_{1-6}$alkyl)amino$C_{1-6}$alkylcarbonyl;
   Alk is $C_{1-6}$alkanediyl and $R^{10}$ is hydrogen;
g) $R^4$ is a radical of formula (c-1) or (c-2) wherein
   $R^{13}$ is hydrogen;
   $R^{14}$ is $C_{1-6}$alkyl;
   $R^{15}$ $C_{1-6}$alkyl;
h) $R^6$ is $C_{1-6}$alkyl, —(CR$^{16}$R$^{17}$)$_p$—$C_{3-10}$cycloalkyl, —$C_{1-6}$alkylCO$_2$R$^{20}$, aminocarbonyl$C_{1-6}$alkyl, -Alk-Ar$^1$ or -AlkHet$^1$;
i) aryl is phenyl.

A particular group of compounds consists of those interesting compounds of formula (I) wherein one or more of the following restrictions apply;
a) $R^1$ is 3-chloro or 3-methyl;
b) $R^2$ is 4-chloro, 4-fluoro or 4-cyano;
c) $R^6$ is methyl or —CH$_2$—C$_{3-10}$cycloalkyl most preferably —CH$_2$-cyclopropyl;
d) $R^{14}$ is methyl.

Another particular group of compounds consists of those compounds of formula (I) wherein one or more of the following restrictions apply:
a) r is 1, s is 1 and t is 0;
b) $R^1$ is halo;
c) $R^2$ is halo, $C_{1-6}$alkyl, $C_{1-6}$alkyloxy or $C_{1-6}$alkyloxycarbonyl;
d) $R^3$ is hydrogen or a radical of formula (b-1) or (b-3) wherein $R^7$ is hydrogen or $C_{1-6}$alkyl, $R^8$ is hydrogen and $R^9$ is hydrogen;
e) $R^4$ is a radical of formula (c-1) or (c-2) wherein $R^{13}$ is hydrogen, $R^{14}$ is $C_{1-6}$alkyl and $R^{15}$ is $C_{1-6}$alkyl;
f) $R^6$ is hydrogen, $C_{1-6}$alkyl, —(CH$_2$)$_p$—C$_{3-10}$cycloalkyl, —$C_{1-6}$alkylCO$_2$C$_{1-6}$alkyl or -Alk-Ar$^1$.

A further particular group of compounds consists of those compounds of formula (I) wherein one or more of the following restrictions apply:
a) r is 1, s is 1 and t is 0;
b) $R^1$ is halo;
c) $R^2$ is halo, $C_{1-6}$alkyl or $C_{1-6}$alkyloxy;
d) $R^3$ is hydrogen, hydroxy or amino;
e) $R^4$ is a radical of formula (c-1) wherein $R^{13}$ is hydrogen and $R^{14}$ is $C_{1-6}$alkyl;
f) $R^6$ is hydrogen or $C_{1-6}$alkyl.

An even further particular group of compounds consists of those compounds of formula (I) wherein $R^1$ is halo, $C_{1-6}$alkyl or forms a bivalent radical of formula (a-1); $R^2$ is halo, cyano, $C_{1-6}$alkyl, or $C_{1-6}$alkyloxy; $R^3$ is hydrogen or a radical of formula (b-1) or (b-3) wherein $R^7$ is hydrogen or -Alk-OR$^{10}$, $R^8$ is hydrogen, $R^9$ is hydrogen or $C_{1-6}$alkylcarbonyl and $R^{10}$ is hydrogen; $R^4$ is a radical of formula (c-1) or (c-2) wherein $R^{13}$ is hydrogen and $R^{14}$ and $R^{15}$ are $C_{1-6}$alkyl; and $R^6$ is hydrogen, $C_{1-6}$alkyl, —CH$_2$—C$_{3-10}$cycloalkyl or —$C_{1-6}$alkylAr$^1$.

Preferred compounds are those compounds of formula (I) wherein $R^1$ is halo, $C_{1-6}$alkyl or forms a bivalent radical of formula (a-1); $R^2$ is halo, cyano, $C_{1-6}$alkyl, or $C_{1-6}$alkyloxy; $R^3$ is hydrogen or a radical of formula (b-1) or (b-3) wherein $R^7$ is hydrogen or -Alk-OR$^{10}$, $R^8$ is hydrogen, $R^9$ is hydrogen or $C_{1-6}$alkylcarbonyl and $R^{10}$ is hydrogen; $R^4$ is a radical of formula (c-1) wherein $R^{13}$ is hydrogen and $R^{14}$ is $C_{1-6}$alkyl; and $R^6$ is hydrogen, $C_{1-6}$alkyl, —CH$_2$—C$_{3-10}$cycloalkyl or —$C_{1-6}$alkylAr$^1$.

More preferred compounds are those compounds of formula (I) wherein r is 1, s is 1 and t is 0; $R^1$ is halo; $R^2$ is halo, $C_{1-6}$alkyl, $C_{1-6}$alkyloxy or $C_{1-6}$alkyloxycarbonyl; $R^3$ is hydrogen or a radical of formula (b-1) or (b-3) wherein $R^7$ is hydrogen or $C_{1-6}$alkyl, $R^8$ is hydrogen and $R^9$ is hydrogen; $R^4$ is a radical of formula (c-1) or (c-2) wherein $R^{13}$ is hydrogen, $R^{14}$ is $C_{1-6}$alkyl and $R^{15}$ is $C_{1-6}$alkyl; and $R^6$ is hydrogen, $C_{1-6}$alkyl, —(CH$_2$)$_p$—C$_{3-10}$cycloalkyl, —$C_{1-6}$alkylCO$_2$C$_{1-6}$alkyl or -Alk-Ar$^1$.

Even more preferred compounds are those compounds of formula (I) wherein r is 1, s is 1 and t is 0; $R^1$ is halo; $R^2$ is halo, $C_{1-6}$alkyl or $C_{1-6}$alkyloxy; $R^3$ is hydrogen, hydroxy or amino; $R^4$ is a radical of formula (c-1) wherein $R^{13}$ is hydrogen and $R^{14}$ is $C_{1-6}$alkyl; and $R^6$ is hydrogen or $C_{1-6}$alkyl.

Most preferred compounds are compounds No 2, No 5, No 19, No 20 and No 23.

compound 2

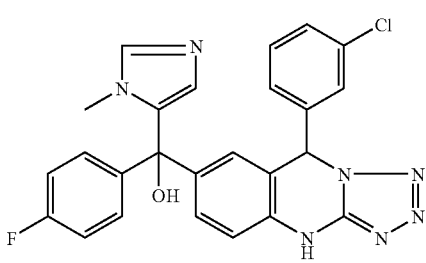

-continued compound 5
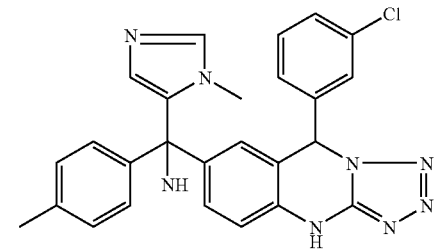

compound 19
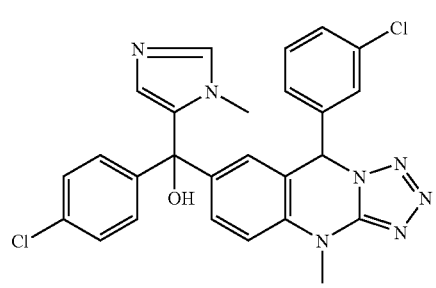

compound 20
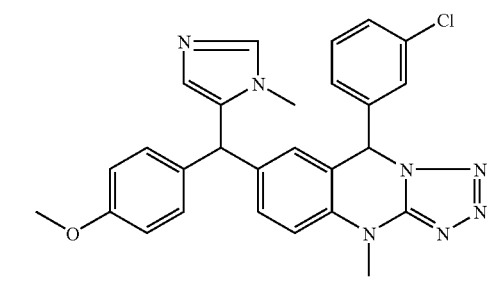

compound 23
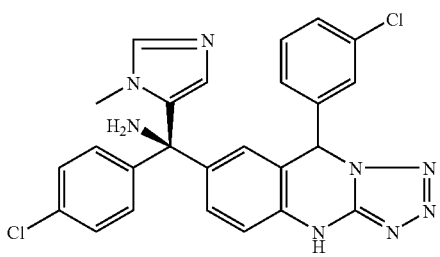

The compounds of formula (I) and their pharmaceutically acceptable salts and N-oxides and stereochemically isomeric forms thereof may be prepared, for example, by the following processes:

a) the compounds of formula (I) wherein $R^4$ represents a radical of formula (c-1), $R^3$ is hydroxy and $R^{14}$ is $C_{1-6}$alkyl, said compounds being referred to as compounds of formula (I-a-1) may be prepared by reacting an intermediate ketone of formula (II) with an intermediate of formula (III-a-1) wherein $R^{14}$ is $C_{1-6}$alkyl. Said reaction requires the presence of a suitable strong base, such as, for example, butyl lithium in an appropriate solvent, such as, for example, tetrahydrofuran, and the presence of an appropriate silane derivative, such as, for example, triethylchlorosilane. During the work-up procedure an intermediate silane derivative is hydrolyzed. Other procedures with protective groups analogues to silane derivatives can also be applied.

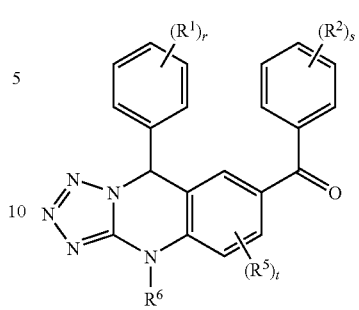
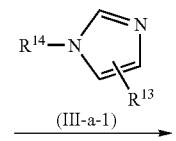

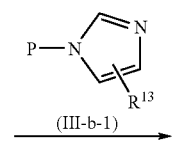

b) the compounds of formula (I), wherein $R^4$ is a radical of formula (c-1), $R^3$ is hydroxy and $R^{14}$ is hydrogen, said compounds being referred to as compounds of formula (I-b-1) may be prepared by reacting an intermediate ketone of formula (II) with an intermediate of formula (III-b-1) wherein P is an optional protective group such as, for example, a sulfonyl group, e.g. a dimethylamino sulfonyl group, which can be removed after the addition reaction. Said reaction requires the presence of a suitable strong base, such as, for example, butyl lithium in an appropriate solvent, such as tetrahydrofuran and the presence of an appropriate silane derivative, such as, for example, triethylchlorosilane. During the work-up procedure an intermediate silane derivative is hydrolyzed. Other procedures with protective groups analogues to silane derivatives can also be applied.

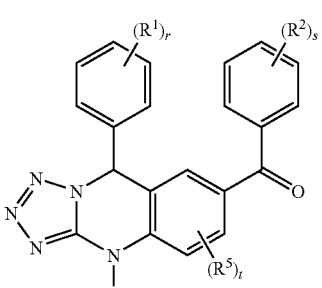

-continued

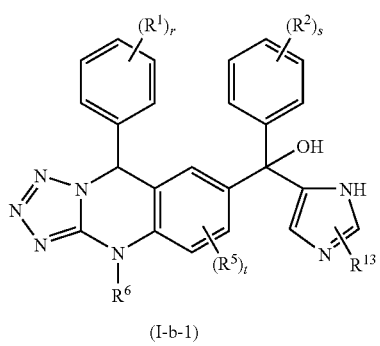

(I-b-1)

c) compounds of formula (I), wherein $R^4$ is a radical of formula (c-2), $R^{15}$ is $C_{1-6}$alkyl and $R^3$ is hydroxy, said compounds being referred to as compounds of formula (I-a-2), may be prepared by reacting an intermediate ketone of formula (II) with an intermediate triazole reagent of formula (III-a-2) wherein $R^{25}$ is hydrogen or $C_{1-6}$alkyl, to form intermediates of formula (IVa-2) and subsequently removing the 3-mercapto or the 3-$C_{1-6}$alkylmercapto group. More in particular, the compounds of formula (I-a-2) may be prepared by reacting the compound of formula (II) with the triazole reagent (III-a-2), preferably in a reaction-inert solvent such as tetrahydrofuran, in the presence of a strong base such as butyl lithium at a temperature ranging from −78° C. to room temperature. Removal of the 3-mercapto group is conveniently effected with sodium nitrite, for example in THF/H$_2$O in the presence of nitric acid. Removal of, for example, the 3-methylmercapto group is conveniently effected with Raney Nickel in ethanol or acetone.

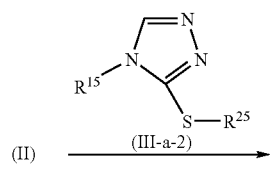

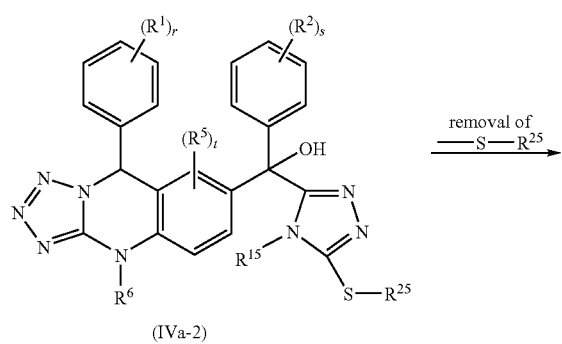

d) Compounds of formula (I), wherein $R^4$ is a radical of formula (c-2), $R^{15}$ is hydrogen and $R^3$ is hydroxy, said compounds being referred to as compounds of formula (I-b-2), may be prepared by reacting an intermediate ketone of formula (II) with an intermediate triazole reagent of formula (III-b-2) wherein P is an optional protective group such as, for example, a sulfonyl group, e.g. a dimethylamino sulfonyl group, which can be removed after the addition reaction. Said reaction requires the presence of a suitable strong base, such as, for example, butyl lithium in an appropriate solvent, such as, for example, tetrahydrofuran. During the work-up procedure an intermediate silane derivative is hydrolyzed. Other procedures with protective groups analogues to silane derivatives can also be applied.

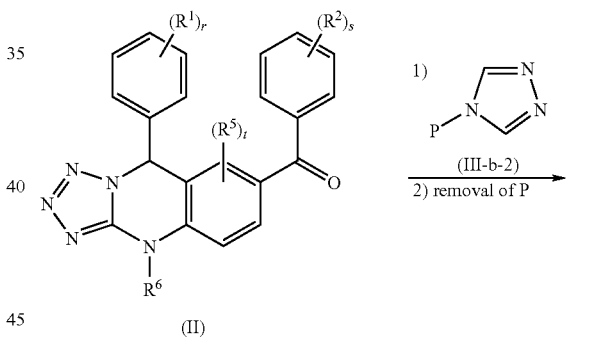

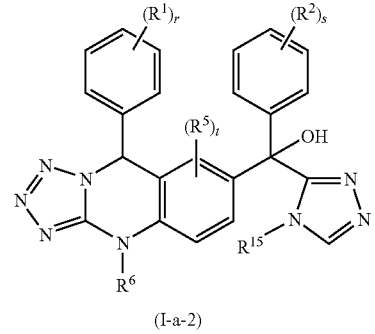

(I-a-2)

Compounds of formula (I-a-1), (I-b-1), (I-a-2) and (1-b-2) can optionally be the subject of one or more of the following conversions in any desired order:

(i) converting a compound of formula (I) into a different compound of formula (I);

(ii) converting a compound of formula (I) into its corresponding pharmaceutically acceptable salt or N-oxide thereof;

(iii) converting a pharmaceutically acceptable salt or N-oxide of a compound of formula (I) into the parent compound of formula (I);

(iv) preparing a stereochemical isomeric form of a compound of formula (I) or a pharmaceutically acceptable salt or N-oxide thereof.

Examples of the conversion of one compound of formula (I) into a different compound of formula (I) include the following reactions:

a) Compounds of formula (I-c) wherein $R^3$ is hydroxy, can be converted into compounds of formula (I-d), defined as a compound of formula (I) wherein $R^3$ is hydrogen, by submitting the compounds of formula (I-c) to appropriate reducing conditions, such as, e.g. stirring in acetic acid in the presence of formamide, or treatment with sodium borohydride/trifluoroacetic acid.

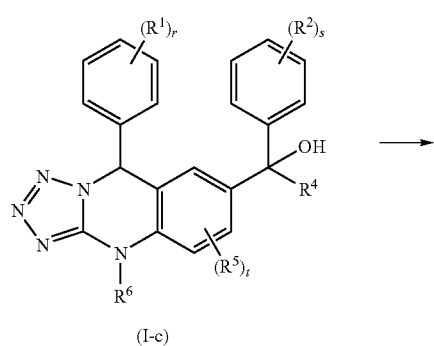

(I-c)

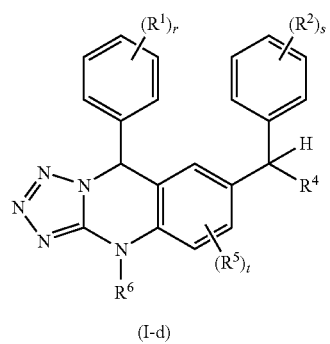

(I-d)

b) Compounds of formula (I-c) can be converted to compounds of formula (I-e) wherein $R^3$ is halo, by reacting the compounds of formula (I-c) with a suitable halogenating agent, such as, e.g. thionyl chloride or phosphorus tribromide. Successively, the compounds of formula (I-e) can be treated with a reagent of formula H—$NR^8R^9$ in a reaction-inert solvent, thereby yielding compounds of formula (I-f).

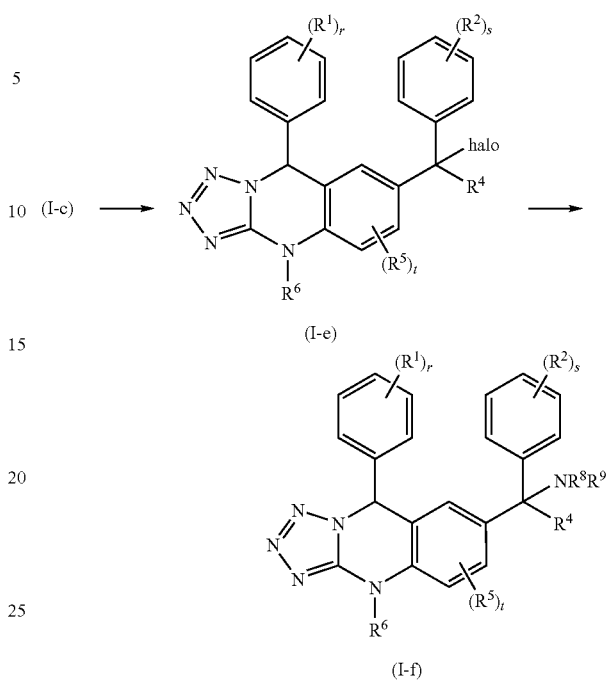

c) Alternatively compounds of formula (I-c) can be converted into compounds of formula (I-f), for example, by treatment with $SOCl_2$, and then $NH_3$/iPrOH, e.g. in a tetrahydrofuran solvent, or by treatment with acetic acid ammonium salt at a temperature ranging from 120 to 180° C., or by treatment with sulfamide at a temperature ranging from 120 to 180° C.

d) The compounds of formula (I) may also be converted into each other via art-known reactions or functional group transformations. A number of such transformations are already described hereinabove. Other examples are hydrolysis of carboxylic esters to the corresponding carboxylic acid or alcohol; hydrolysis of amides to the corresponding carboxylic acids or amines; hydrolysis of nitriles to the corresponding amides; amino groups on imidazole or phenyl may be replaced by a hydrogen by art-known diazotation reactions and subsequent replacement of the diazo-group by hydrogen; alcohols may be converted into esters and ethers; primary amines may be converted into secondary or tertiary amines; double bonds may be hydrogenated to the corresponding single bond; an iodo radical on a phenyl group may be converted in to an ester group by carbon monoxide insertion in the presence of a suitable palladium catalyst.

The intermediates and starting materials used in the above-described processes may be prepared in conventional manner using procedures known in the art for example as described in the above-mentioned patent specifications WO 97/16443, WO 97/21701, WO 98/40383, WO 98/49157 and WO 00/39082.

For example intermediates of formula (V) can be prepared by procedures described in International Patent Specification No. WO 00/39082, from page 9 to page 15, or by processes analogues thereto. Intermediates of formula (V) can be further converted in compounds of formula (I) wherein $R^6$ is hydrogen said compounds being referred to as compounds of formula (I-g) by heating at 120° C. in an appropriate solvent such as toluene.

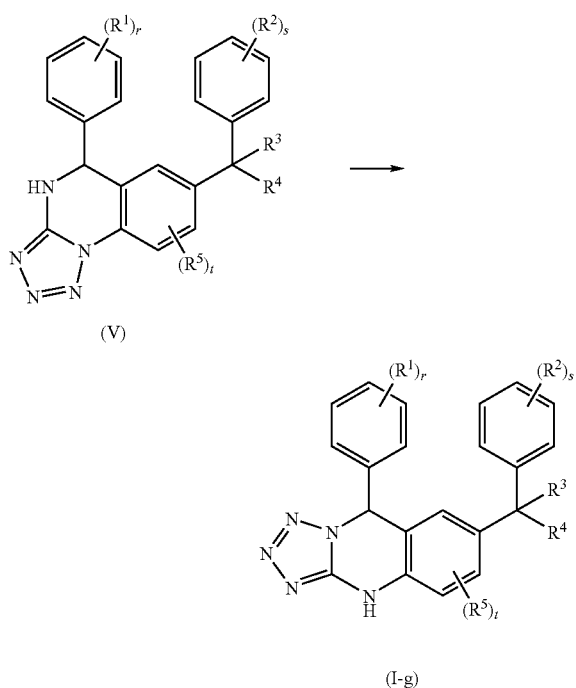

(V)

(I-g)

In a similar way intermediates of formula (VI) can be converted in intermediates of formula (VII).

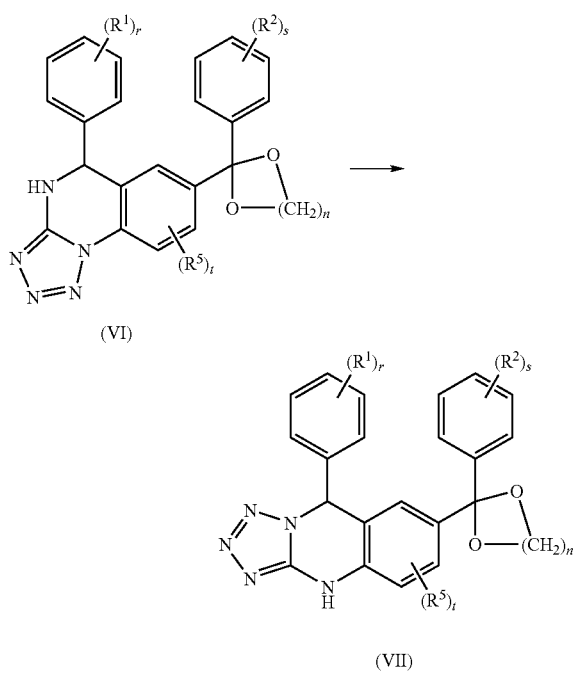

(VI)

(VII)

The preparation of intermediates of formula (VI) and the further conversion of the intermediates of formula (VII) can be preformed as described in International Patent Specification No. WO 98/49157, from page 11 to page 13, and in International Patent Specification No. WO 00/39082, from page 9 to page 15, or by processes analogues thereto.

The compounds of formula (I) and some of the intermediates have at least one stereogenic center in their structure. This stereogenic center may be present in a R or a S configuration.

The compounds of formula (I) as prepared in the hereinabove described processes are generally racemic mixtures of enantiomers which can be separated from one another following art-known resolution procedures. The racemic compounds of formula (I) may be converted into the corresponding diastereomeric salt forms by reaction with a suitable chiral acid. Said diastereomeric salt forms are subsequently separated, for example, by selective or fractional crystallization and the enantiomers are liberated therefrom by alkali. An alternative manner of separating the enantiomeric forms of the compounds of formula (I) involves liquid chromatography using a chiral stationary phase. Said pure stereochemically isomeric forms may also be derived from the corresponding pure stereochemically isomeric forms of the appropriate starting materials, provided that the reaction occurs stereospecifically. Preferably if a specific stereoisomer is desired, said compound will be synthesized by stereospecific methods of preparation. These methods will advantageously employ enantiomerically pure starting materials.

The compounds of formula (I), the pharmaceutically acceptable acid addition salts and stereoisomeric forms thereof have valuable pharmacological properties in that they have a potent farnesyl protein transferase (FPTase) inhibitory effect.

This invention provides a method for inhibiting the abnormal growth of cells, including transformed cells, by administering an effective amount of a compound of the invention. Abnormal growth of cells refers to cell growth independent of normal regulatory mechanisms (e.g. loss of contact inhibition). This includes the abnormal growth of: (1) tumor cells (tumors) expressing an activated ras oncogene; (2) tumor cells in which the ras protein is activated as a result of oncogenic mutation of another gene; (3) benign and malignant cells of other proliferative diseases in which aberrant ras activation occurs. Furthermore, it has been suggested in literature that ras oncogenes not only contribute to the growth of tumors in vivo by a direct effect on tumor cell growth but also indirectly, i.e. by facilitating tumor-induced angiogenesis (Rak. J. et al, *Cancer Research*, 55, 4575-4580, 1995). Hence, pharmacologically targeting mutant ras oncogenes could conceivably suppress solid tumor growth in vivo, in part, by inhibiting tumor-induced angiogenesis.

This invention also provides a method for inhibiting tumor growth by administering an effective amount of a compound of the present invention, to a subject, e.g. a mammal (and more particularly a human) in need of such treatment. In particular, this invention provides a method for inhibiting the growth of tumors expressing an activated ras oncogene by the administration of an effective amount of the compounds of the present invention. Examples of tumors which may be inhibited, but are not limited to, lung cancer (e.g. adenocarcinoma and including non-small cell lung cancer), pancreatic cancers (e.g. pancreatic carcinoma such as, for example exocrine pancreatic carcinoma), colon cancers (e.g. colorectal carcinomas, such as, for example, colon adenocarcinoma and colon adenoma), prostate cancer including the advanced disease, hematopoietic tumors of lymphoid lineage (e.g. acute lymphocytic leukemia, B-cell lymphoma, Burkitt's lymphoma), myeloid leukemias (for example, acute myelogenous leukemia (AML)), thyroid follicular cancer, myelodysplastic syndrome (MDS), tumors of mesenchymal origin (e.g. fibrosarcomas and rhabdomyosarcomas), melanomas, teratocarcinomas, neuroblastomas, gliomas, benign tumor of the skin (e.g. keratoacanthomas), breast carcinoma (e.g. advanced breast cancer), kidney carcinoma, ovary carcinoma, bladder carcinoma and epidermal carcinoma.

This invention may also provide a method for inhibiting proliferative diseases, both benign and malignant, wherein ras proteins are aberrantly activated as a result of oncogenic mutation in genes. With said inhibition being accomplished by the administration of an effective amount of the compounds described herein, to a subject in need of such a treatment. For example, the benign proliferative disorder neurofibromatosis, or tumors in which ras is activated due to mutation or overexpression of tyrosine kinase oncogenes, may be inhibited by the compounds of this invention.

The compound according to the invention can be used for other therapeutic purposes, for example:
a) the sensitisation of tumors to radiotherapy by administering the compound according to the invention before, during or after irradiation of the tumor for treating cancer, for example as described in WO 00/01411;
b) treating athropathies such as rheumatoid arthritis, osteoarthritis, juvenile arthritis, gout, polyarthritis, psoriatic arthritis, ankylosing spondylitis and systemic lupus erythematosus, for example as described in WO 00/01386;
c) inhibiting smooth muscle cell proliferation including vascular proliferative disorders, atherosclerosis and restenosis, for example as described in WO 98/55124;
d) treating inflammatory conditions such as ulcerative colitis, Crohn's disease, allergic rhinitis, graft vs host disease, conjunctivitis, asthma, ARDS, Behcets disease, transplant rejection, uticaria, allergic dermatitis, alopecia greata, scleroderma, exanthem, eczema, dermatomyositis, acne, diabetes, systemic lupus erythematosis, Kawasaki's disease, multiple sclerosis, emphysema, cystic fibrosis and chronic bronchitis;
e) treating endometriosis, uterine fibroids, dysfunctional uterine bleeding and endometrial hyperplasia;
f) treating ocular vascularisation including vasculopathy affecting retinal and choroidal vessels;
g) treating pathologies resulting from heterotrimeric G protein membrane fixation including diseases related to following biological functions or disorders; smell, taste, light, perception, neurotransmission, neurodegeneration, endocrine and exocrine gland functioning, autocrine and paracrine regulation, blood pressure, embryogenesis, viral infections, immunological functions, diabetes, obesity;
h) inhibiting viral morphogenesis for example by inhibiting the prenylation or the post-prenylation reactions of a viral protein such as the large delta antigen of hepatitis D virus; and the treatment of HIV infections;
i) treating polycystic kidney disease;
j) suppressing induction of inducible nitric oxide including nitric oxide or cytokine mediated disorders, septic shock, inhibiting apoptosis and inhibiting nitric oxide cytotoxicity;
k) treating malaria.

The compounds of present invention may be particularly useful for the treatment of proliferative diseases, both benign and malignant, wherein the K-ras B isoform is activated as a result of oncogenic mutation.

Hence, the present invention discloses the compounds of formula (I) for use as a medicine as well as the use of these compounds of formula (I) for the manufacture of a medicament for treating one or more of the above mentioned conditions.

For the treatment of the above conditions, the compound of the invention may be advantageously employed in combination with one or more other medicinal agents such as anti-cancer agents for example selected from platinum coordination compounds for example cisplatin or carboplatin, taxane compounds for example paclitaxel or docetaxel, camptothecin compounds for example irinotecan or topotecan, anti-tumor vinca alkaloids for example vinblastine, vincristine or vinorelbine, anti-tumor nucleoside derivatives for example 5-fluorouracil, gemcitabine or capecitabine, nitrogen mustard or nitrosourea alkylating agents for example cyclophosphamide, chlorambucil, carrnustine or lomustine, anti-tumor anthracycline derivatives for example daunorubicin, doxorubicin or idarubicin; HER2 antibodies for example trastzumab; and anti-tumor podophyllotoxin derivatives for example etoposide or teniposide; and antiestrogen agents including estrogen receptor antagonists or selective estrogen receptor modulators preferably tamoxifen, or alternatively toremifene, droloxifene, faslodex and raloxifene, or aromatase inhibitors such as exemestane, anastrozole, letrazole and vorozole.

For the treatment of cancer the compounds according to the present invention can be administered to a patient as described above, in conjunction with irradiation. Such treatment may be especially beneficial, as farnesyl transferase inhibitors can act as radiosensitisers, for example as described in International Patent Specification WO 00/01411, enhancing the therapeutic effect of such irradiation.

Irradiation means ionizing radiation and in particular gamma radiation, especially that emitted by linear accelerators or by radionuclides that are in common use today. The irradiation of the tumor by radionuclides can be external or internal.

Preferably, the administration of the farnesyl transferase inhibitor commences up to one month, in particular up to 10 days or a week, before the irradiation of the tumor. Additionally, it is advantageous to fractionate the irradiation of the tumor and maintain the administration of the farnesyl transferase inhibitor in the interval between the first and the last irradiation session.

The amount of farnesyl protein transferase inhibitor, the dose of irradiation and the intermittence of the irradiation doses will depend on a series of parameters such as the type of tumor, its location, the patient's reaction to chemo- or radio-therapy and ultimately is for the physician and radiologists to determine in each individual case.

The present invention also concerns a method of cancer therapy for a host harboring a tumor comprising the steps of
administering a radiation-sensitizing effective amount of a farnesyl protein transferase inhibitor according to the invention before, during or after
administering radiation to said host in the proximity to the tumor.

In view of their useful pharmacological properties, the subject compounds may be formulated into various pharmaceutical forms for administration purposes.

To prepare the pharmaceutical compositions of this invention, an effective amount of a particular compound, in base or acid addition salt form, as the active ingredient is combined in intimate admixture with a pharmaceutically acceptable carrier, which carrier may take a wide variety of forms depending on the form of preparation desired for administration. These pharmaceutical compositions are desirably in unitary dosage form suitable, preferably, for administration orally, rectally, percutaneously, or by parenteral injection. For example, in preparing the compositions in oral dosage form, any of the usual pharmaceutical media may be employed, such as, for example, water, glycols, oils, alcohols and the like in the case of oral liquid preparations such as suspensions, syrups, elixirs and solutions; or solid carriers such as starches, sugars, kaolin, lubricants, binders, disintegrating agents and the like in the case of powders, pills, capsules and tablets.

Because of their ease in administration, tablets and capsules represent the most advantageous oral dosage unit form, in which case solid pharmaceutical carriers are obviously employed. For parenteral compositions, the carrier will usually comprise sterile water, at least in large part, though other ingredients, to aid solubility for example, may be included. Injectable solutions, for example, may be prepared in which the carrier comprises saline solution, glucose solution or a mixture of saline and glucose solution. Injectable suspensions may also be prepared in which case appropriate liquid carriers, suspending agents and the like may be employed. In the compositions suitable for percutaneous administration, the carrier optionally comprises a penetration enhancing agent and/or a suitable wetting agent, optionally combined with suitable additives of any nature in minor proportions, which additives do not cause a significant deleterious effect to the skin. Said additives may facilitate the administration to the skin and/or may be helpful for preparing the desired compositions. These compositions may be administered in various ways, e.g., as a transdermal patch, as a spot-on or as an ointment.

It is especially advantageous to formulate the aforementioned pharmaceutical compositions in dosage unit form for ease of administration and uniformity of dosage. Dosage unit form as used in the specification and claims herein refers to physically discrete units suitable as unitary dosages, each unit containing a predetermined quantity of active ingredient, calculated to produce the desired therapeutic effect, in association with the required pharmaceutical carrier. Examples of such dosage unit forms are tablets (including scored or coated tablets), capsules, pills, powder packets, wafers, injectable solutions or suspensions, teaspoonfuls, tablespoonfuls and the like, and segregated multiples thereof.

Those skilled in the art could easily determine the effective amount from the test results presented hereinafter. In general it is contemplated that a therapeutically effective amount would be from 0.001 mg/kg to 100 mg/kg body weight, and in particular from 0.5 mg/kg to 100 mg/kg body weight. It may be appropriate to administer the required dose as two, three, four or more sub-doses at appropriate intervals throughout the day. Said sub-doses may be formulated as unit dosage forms, for example, containing 0.5 to 500 mg, and in particular 10 mg to 500 mg of active ingredient per unit dosage form.

EXPERIMENTAL PART

The following examples are provided for purposes of illustration.

Hereinafter "BTEAC" means benzyltriethylammonium salt, "BuLi" means n-butyl lithium, "DCM" means dichloromethane, 'DIPE' means diisopropyl ether, "DMA" means N,N-dimethyl-acetamide, "DMF" means N,N-dimethylformamide, 'DMSO' means dimethylsulfoxide, 'EtOH' means ethanol, 'EtOAc' means ethyl acetate, 'iPrOH' means isopropanol, 'MeOH' means methanol, 'THF' means tetrahydrofuran, and 'mp' means melting point, 'kromasil®' is a spherical, totally silica-based chromatographic packing material developed by Eka Nobel in Sweden, 'diastereoisomer (A)' is the first fraction that is eluted after normal chromatography of a diastereoisomeric mixture, 'diastereoisomer (B)' is the second fraction that is eluted after normal chromatography of a diastereoisomeric mixture.

A. Preparation of the Intermediates

EXAMPLE A1 a) nBuLi 1.6M in hexane (0.112 mol) was added dropwise at −70° C. under $N_2$ flow to a mixture of 5-bromo-3-(3-chlorophenyl)-2,1-benzisoxazole (0.097 mol) in THF (300 ml). The mixture was stirred at −70° C. for 15 min. A mixture of 4-fluorobenzaldehyde (0.112 mol) in THF (100 ml) was added dropwise. The mixture was stirred at −70° C. for 30 min, then hydrolized and extracted with EtOAc. The organic layer was separated, dried ($MgSO_4$), filtered and the solvent was evaporated till dryness. The residue was taken up in diethyl ether and DIPE. The precipitate was filtered off, washed and dried, yielding 9.2 g (26.8%) of 3-(3-chlorophenyl)-α-(4-fluorophenyl)-2,1-benzisoxazole-5-methanol (intermediate 1), mp. 171° C.

b) A mixture of intermediate 1 (0.0514 mol) and $MnO_2$ (18 g) in 1,4-dioxane (200 ml) was stirred at 80° C. for 3 hours, then cooled to room temperature and filtered over celite. The solvent was evaporated till dryness. The product was used without further purification, yielding (quant.) of [3-(3-chlorophenyl)-2,1-benzisoxazol-5-yl](4-fluorophenyl)-methanone (intermediate 2), mp. 165° C.

c) A mixture of intermediate 2 (0.0514 mol) in THF (180 ml) was cooled on an ice bath. $TiCl_3$ 15% in water (180 ml) was added dropwise slowly. The mixture was stirred at room temperature overnight, then poured out into ice water and extracted with DCM. The organic layer was separated, dried ($MgSO_4$), filtered and the solvent was evaporated till dryness, yielding 18.2 g (100%) of [2-amino-5-(4-fluorobenzoyl)phenyl](3-chlorophenyl)-methanone (intermediate 3).

d) Trichloro-acetylchloride (0.0848 mol) was added dropwise at 5° C. to a mixture of intermediate 3 (0.0707 mol) in DCM (250 ml) under $N_2$ flow. The mixture was stirred at 5° C. for 30 minutes. Triethylamine (0.0848 mol) was added dropwise at 5° C. The mixture was stirred at 5° C. for 1 hour, then at room temperature for 2 hours and poured out into ice water. DCM was added. The mixture was extracted with DCM. The organic layer was separated, dried ($MgSO_4$), filtered and the solvent was evaporated. The residue was crystallized from diethyl ether/DIPE. The precipitate was filtered off and dried, yielding 33.7 g (95%) of 2,2,2-trichloro-N-[2-(3-chlorobenzoyl)-4-(4-fluorobenzoyl)phenyl]-acetamide (intermediate 4).

e) Acetic acid, ammonium salt (0.135 mol) was added at room temperature to a mixture of intermediate 4 (0.0675 mol) in DMSO (300 ml). The mixture was stirred at 60° C. for 4 hours, then brought to room temperature and poured out into water. The precipitate was filtered, washed with water, taken up in warm $CH_3CN$, filtered, washed again with $CH_3CN$, then with diethyl ether and dried under a vacuo, yielding 18.5 g (72%) of intermediate 5. The mother layer was purified by column chromatography over silica gel (15-40 μm) (eluent: DCM/MeOH:$NH_4OH$ 95/5/0.1). The pure fractions were collected and the solvent was evaporated. The residue was crystallized from 2-propanone/diethyl ether. The precipitate was filtered off and dried, yielding 1.8 g (7%) of 4-(3-chlorophenyl)-6-(4-fluorobenzoyl)-2(1H)-quinazolinone (intermediate 5), mp. 226° C.

f) Intermediate 5 (0.0528 mol) was added in phosphoryl chloride (200 ml) at room temperature. The mixture was stirred at 100° C. for 3 hours and cooled to room temperature. The solvent was evaporated. The residue was taken up in DCM. The solvent was evaporated till dryness. The residue was taken up in DCM, poured out into ice water, neutralised with $K_2CO_3$ solid and extracted with DCM. The organic layer was washed with water, separated, dried (MgSO$_4$), filtered, and the solvent was evaporated. The residue was crystallized from 2-propanone. The precipitate was filtered off and dried, yielding 8.5 g (40%) of intermediate 6. The mother layer was evaporated. The residue was purified by column chromatography over silica gel (eluent: toluene/EtOAc 95/5; 15-35 μm). The pure fractions were collected and the solvent was evaporated. A part (0.5 g) of the residue (8.9 g, 42%) was crystallized from 2-propanone. The precipitate was filtered off and dried, yielding 0.3 g of [2-chloro-4-(3-chlorophenyl)-6-quinazolinyl](4-fluorophenyl)-methanone (intermediate 6), mp. 138° C.

g) BuLi 1.6M in hexane (46.5 ml, 0.0744 mol) was added dropwise at −70° C. to a mixture of 1-methyl-1H-imidazole (0.0744 mol) in THF (70 ml) under N$_2$ flow. Chlorotriethylsilane (0.0765 mol) was added dropwise at −70° C. The mixture was stirred at −70° C. for 15 minutes. BuLi 1.6M in hexane (41 ml, 0.0659 mol) was added dropwise at −70° C. The mixture was stirred at −70° C. for 15 minutes. A solution of intermediate 6 (0.0425 mol) in THF (150 ml) was added dropwise at −70° C. The mixture was stirred at −70° C. for 1 hour and poured out into water. EtOAc was added. The mixture was extracted with EtOAc. The organic layer was washed twice with water, separated, dried (MgSO$_4$), filtered and the solvent was evaporated. The residue was purified by column chromatography over silica gel (15-35 μm) (eluent: DCM/MeOH/NH$_4$OH 97/3/0.5). The pure fractions were collected and the solvent was evaporated. Part (0.5 g) of the residue (14.6 g, 72%) was crystallized from 2-propanone/CH$_3$CN. The precipitate was filtered off and dried under a vacuo, yielding 0.17 g of 2-chloro-4-(3-chlorophenyl)-α-(4-fluorophenyl)-α-(1-methyl-1H-imidazol-5-yl)-6-quinazolinemethanol (intermediate 7), mp. 212° C.

h) A mixture of intermediate 7 (0.0125 mol) and sodium azide (0.038 mol) in DMF (60 ml) was stirred at 90° C. for 2 hours, then brought to room temperature, poured out into ice water and stirred. The precipitate was filtered, washed with water, taken up in DCM, filtered, washed with diethyl ether and dried under a vacuo, yielding 3.5 g (58%) of intermediate 8. The filtrate was extracted with DCM. The organic layer was separated, dried (MgSO$_4$), filtered, and the solvent was evaporated. The residue was purified by column chromatography over silica gel (15-40 μm) (eluent: DCM/MeOH/NH$_4$OH 95/5/0.1). The pure fractions were collected and the solvent was evaporated. The residue (0.9 g, 15%) was crystallized from 2-propanone. The precipitate was filtered off and dried, yielding 0.7 g (12%) of 5-(3-chlorophenyl)-α-(4-fluorophenyl)-α-(1-methyl-1H-imidazol-5-yl)-tetrazolo[1,5-a]quinazoline-7-methanol (intermediate 8), mp. 200° C.

i) Sodium hydroborate (0.001 mol) was added portionwise at room temperature to a mixture of intermediate 8 (0.001 mol) in methanol (5 ml). The mixture was stirred at room temperature for 2 hours and poured out into ice water. DCM was added. The organic layer was washed with water, separated, dried (MgSO$_4$), filtered and the solvent was evaporated. The residue was crystallized from 2-propanone. The precipitate was filtered off and dried in a vacuo. The residue (0.35 g, 70%) was crystallized from ethanol. The precipitate was filtered off and dried in a vacuo, yielding 0.105 g (21%) of 5-(3-chlorophenyl)-α-(4-fluorophenyl)-4,5-dihydro-α-(1-methyl-1H-imidazol-5-yl)-tetrazolo[1,5-a]quinazoline-7-methanol (intermediate 9), mp. 230° C.

EXAMPLE A2 a) 5-bromo-3-(3-chlorophenyl)-2,1-benzisoxazole (0.13 m) was added at −70° C. to THF (300 ml) under N$_2$ flow. A solution of BuLi (0.143 mol) was added dropwise. The mixture was stirred at −70° C. for 10 minutes. A solution of N,4-dimethoxy-N-methylbenzamide (0.117 mol) in THF (100 ml) was added dropwise at −70° C. The mixture was stirred at −70° C. for 1 hour, poured out on ice/EtOAc and extracted with EtOAc. The organic layer was separated, dried (MgSO$_4$), filtered, and the solvent was evaporated. The residue was crystallized from diethyl ether. The precipitate was filtered off and dried under a vacuo, yielding 19.5 g (41%) of [3-(3-chlorophenyl)-2,1-benzisoxazol-5-yl](4-methoxyphenyl)-methanone (intermediate 10).

b) Intermediate 10 (0.0536 mol) was added at room temperature to THF (200 ml). TiCl$_3$ 15% in water (120 ml) was added dropwise at room temperature. The mixture was stirred at room temperature for 3 hours, poured out into ice water and extracted with DCM. The organic layer was separated, washed with K$_2$CO$_3$ 10% then with water, dried (MgSO$_4$), filtered and the solvent was evaporated, yielding 20.5 g (quantitative) of [2-amino-5(4-methoxybenzoyl)phenyl](3-chlorophenyl)-methanone (intermediate 11).

c) A mixture of intermediate 11 (0.0536 mol) in DCM (200 ml) was cooled to 5° C. under N$_2$ flow. A solution of trichloroacetylchloride (0.0643 mol) was added dropwise at 5° C. The mixture was stirred at 5° C. for 30 minutes. A solution of triethylamine (0.0643 mol) was added dropwise at 5° C. The mixture was stirred at 5° C. for 1 hour then at room temperature for 2 hours, poured out into ice water and extracted with DCM. The organic layer was separated, washed with water, dried (MgSO$_4$), filtered and the solvent was evaporated, yielding 27.4 g (quantitative) of 2,2,2-trichloro-N-[2-(3-chlorobenzoyl)-4-(4-methoxybenzoyl)phenyl]-acetamide (intermediate 12).

d) Acetic acid, ammonium salt (0.107 mol) was added at room temperature to a mixture of intermediate 12 (0.0536 mol) in DMSO (250 ml). The mixture was stirred at 60° C. for 4 hours then brought to room temperature, poured out into ice water and stirred. The precipitate was filtered, washed with water and taken up in warm CH$_3$CN. The precipitate was filtered, washed with diethyl ether and dried under a vacuo, yielding 16.2 g (77%) of intermediate 13. The mother layer was evaporated. The residue was purified by column chromatography over silica gel (15-40 μm) (eluent: DCM/MeOH/NH$_4$OH; 95/5/0.1). The pure fractions were collected and the solvent was evaporated. The residue (1.2 g, 6%) was crystallized from 2-propanone. The precipitate was filtered off and dried, yielding 0.9 g (4%) of 4-(3-chlorophenyl)-6-(4-methoxybenzoyl)-2(1H)quinazolinone (intermediate 13), mp. 248° C.

e) Intermediate 13 (0.0432 mol) was added at room temperature to phosphoryl chloride (150 ml). The mixture was stirred at 100° C. for 3 hours then brought to room temperature. The solvent was evaporated till dryness. The residue was taken up in DCM. The solvent was evaporated. The residue was taken up in DCM. The mixture was poured out into ice water, neutralized with K$_2$CO$_3$ solid and extracted with DCM. The organic layer was separated, washed with water, dried (MgSO$_4$), filtered and the solvent was evaporated. The residue was crystallized from CH$_3$CN. The precipitate was filtered off and dried under a vacuo, yielding 15.5 g (87%) of intermediate 14. The mother layer was purified by column chromatography over silica gel (eluent: toluene/EtOAc; 9317; 15-40 μm). The pure fractions were collected and the solvent was evaporated. The residue (0.7 g, 4%) was crystallized from 2-propanone. The precipitate was filtered off and dried under a vacuo, yielding 0.5 g (3%) of [2-chloro-4-(3-chlorophenyl)-6-quinazolinyl](4-methoxyphenyl)-methanone (intermediate 14), mp. 175° C.

f) nBuLi (0.0665 mol) was added dropwise at −70° C. to a solution of 1-methyl-1H-imidazole (0.0665 mol) in THF (60 ml) under $N_2$ flow. The mixture was stirred for 15 minutes. Chlorotriethyl-silane (0.0684 mol) was added dropwise. The mixture was stirred for 15 minutes. nBuli (0.059 mol) was added dropwise. The mixture was stirred for 15 minutes. A solution of intermediate 14 (0.038 mol) in THF (150 ml) was added at −70° C. The mixture was stirred at −70° C. for 1 hour and poured out into water. EtOAc was added. The mixture was extracted with EtOAc. The organic layer was washed with water, separated, dried ($MgSO_4$), filtered, and the solvent was evaporated. The residue was purified by column chromatography over silica gel (15-35 µm) (eluent: DCM/MeOH/$NH_4$OH 96/4/0.2). The pure fractions were collected and the solvent was evaporated, yielding 11 g (59%) of 2-chloro-4-(3-chlorophenyl)-α-(4-methoxyphenyl)-α-(1-methyl-1H-imidazol-5-yl)-6-quinazolinemethanol (intermediate 15).

g) A mixture of intermediate 15 (0.0224 mol) and sodium azide (0.067 mol) in DMF (120 ml) was stirred at 90° C. for 2 hours, brought to room temperature, poured out into ice water and stirred. The precipitate was filtered, washed with water and taken up in DCM. The organic layer was washed with water, separated, dried ($MgSO_4$), filtered, and the solvent was evaporated. The residue was purified by column chromatography over silica gel (15-40 µm) (eluent: toluene/iPrOH/$NH_4$OH 90/10/1). The pure fractions were collected and the solvent was evaporated, yielding 9 g (80%) of 5-(3-chlorophenyl)-α-(4-methoxyphenyl)-α-(1-methyl-1H-imidazol-5-yl)-tetrazolo[1,5-a]quinazoline-7-methanol (intermediate 16), mp 200° C.

h) $NaBH_4$ (0.003 mol) was added portionwise at room temperature to a mixture of intermediate 16 (0.003 mol) in methanol (15 ml). The mixture was stirred at room temperature for 2 hours and poured out into ice water. DCM was added. The mixture was extracted with DCM. The organic layer was separated, dried ($MgSO_4$), filtered, and the solvent was evaporated. The residue (1.3 g, 86%) was crystallized from 2-propanone/diethyl ether. The precipitate was filtered off and dried, yielding 1 g (67%) of 5-(3-chlorophenyl)-4,5-dihydro-α-(4-methoxyphenyl)-α-(1-methyl-1H-imidazol-5-yl)-tetrazolo[1,5-a]quinazoline-7-methanol (intermediate 17), mp. 220° C.

EXAMPLE A3 a) nBuLi 1.6 M in hexane (0.112 mol) was added dropwise at −70° C. under $N_2$ flow to a mixture of 5-bromo-3-(3-chlorophenyl)-2,1-benzisoxazole (0.097 mol) in THF (300 ml). The mixture was stirred at −70° C. for 15 min. A mixture of 4-methylbenzaldehyde (0.112 mol) in THF (100 ml) was added dropwise. The mixture was stirred at −70° C. for 30 min, then hydrolized and extracted with EtOAc. The organic layer was separated, dried ($MgSO_4$), filtered and the solvent was evaporated till dryness. The residue was purified by column chromatography over silica gel (20-45 µm) (eluent: DCM/EtOAc 96/4). The pure fractions were collected and the solvent was evaporated, yielding 13 g (38.3%) of 3-(3-chlorophenyl)-α-(4-methylphenyl)-2,1-benzisoxazole-5-methanol (intermediate 18).

b) A mixture of intermediate 18 (0.071 mol) and $MnO_2$ (0.287 mol) in 1,4-dioxane (250 ml) was stirred at 80° C. for 2 hours, then cooled to room temperature, filtered over celite and washed with DCM. The solvent was evaporated till dryness, yielding 24.7 g (100%) of [3-(3-chlorophenyl)-2,1-benzisoxazol-5-yl](4-methylphenyl)-methanone (intermediate 19).

c) A mixture of intermediate 19 (0.071 mol) in THF (250 ml) was cooled on an ice bath. $TiCl_3$ 15% in water (250 ml) was added dropwise. The mixture was stirred at room temperature overnight, then poured out into ice water and extracted with DCM. The organic layer was separated, dried ($MgSO_4$), filtered and the solvent was evaporated till dryness, yielding 20.5 g (82.6%) of [2-amino-5(4-methylbenzoyl)phenyl](3-chlorophenyl)-methanone (intermediate 20).

d) Intermediate 20 (0.0085 mol) was added at 5° C. to DCM (30 ml) under $N_2$ flow. trichloro-acetyl chloride (0.01 mol) then triethylamine (0.01 mol) were added dropwise. The mixture was brought to room temperature, stirred at room temperature for 3 hours, poured out into ice water and extracted with DCM. The organic layer was separated, dried ($MgSO_4$), filtered, and the solvent was evaporated, yielding 4.2 g (quantitative) of 2,2,2-trichloro-N-[2-(3-chlorobenzoyl)-4-(4-methylbenzoyl)phenyl]-acetamide (intermediate 21).

e) A mixture of intermediate 21 (0.0085 mol) and acetic acid, ammonium salt (0.0169 mol) in DMSO (42 ml) was stirred at 60° C. for 4 hours then cooled and poured out into ice water. The precipitate was filtered, washed with water, taken up in warm $CH_3CN$, filtered off and dried under a vacuo, yielding 2.02 g (63%) of 4-(3-chlorophenyl)-6-(4-methylbenzoyl)-2(1H)quinazolinone (intermediate 22), mp. >260° C.

f) A mixture of intermediate 22 (0.041 mol) in phosphoryl chloride (105 ml) was stirred at 100° C. for 4 hours then cooled. The solvent was evaporated. The residue was taken up DCM. The solvent was evaporated. The residue was taken up in DCM. The mixture was poured out into ice water, basified with $K_2CO_3$ 10% and extracted. The organic layer was separated, washed with water, dried ($MgSO_4$), filtered and the solvent was evaporated. The residue was crystallized from $CH_3CN$. The precipitate was filtered off and dried, yielding 11.4 g (70%) of intermediate 23. The mother layer was evaporated and purified by column chromatography over silica gel (eluent: cyclohexane/EtOAc; 90/10; 15-40 µm). The pure fractions were collected and the solvent was evaporated, yielding 1.7 g (10.5%) of [2-chloro-4-(3-chlorophenyl)-6-quinazolinyl](4-methylphenyl)-methanone (intermediate 23), mp. 156° C.

g) 1-Methyl-1H-imidazole (0.0507 mol) was added at −70° C. to THF (90 ml) under $N_2$ flow. nBuLi (31.5 ml) was added dropwise. The mixture was stirred at −70° C. for 15 minutes. Chlorotriethyl-silane (0.0522 mol) was added dropwise. The mixture was stirred at −70° C. for 15 minutes. nBuLi (28 ml) was added. The mixture was stirred at −70° C. for 15 minutes. A mixture of intermediate 23 (0.029 mol) in THF (115 ml) was added dropwise. The mixture was stirred at −70° C. for 1 hour, poured out into water and extracted with DCM. The organic layer was separated, washed with water, dried ($MgSO_4$), filtered and the solvent was evaporated. The residue was purified by column chromatography over silica gel (15-35 µm) (eluent: DCM/MeOH/$NH_4$OH; 96/4/0.1). The pure fractions were collected and the solvent was evaporated, yielding 9 g (65%). A sample (0.3 g) was crystallized from 2-propanone, The precipitate was filtered off and dried, yielding 2-chloro-4-(3-chlorophenyl)-α-(1-methyl-1H-imidazol-5-yl)-α-(4-methylphenyl)-6-quinazolinemethanol (intermediate 24), mp. 220° C.

h) A mixture of intermediate 24 (0.0105 mol) and sodium azide (0.031 mol) in DMF (70 ml) was stirred at 90° C. for 2 hours then cooled and poured out into ice water. The precipitate was filtered and taken up in DCM. The organic layer was washed with water, separated, dried (MgSO$_4$), filtered, and the solvent was evaporated. The residue was purified by column chromatography over silica gel (15-40 μm) (eluent: DCM/MeOH/NH$_4$OH; 95/5/0.1). The pure fractions were collected and the solvent was evaporated, yielding 3.68 g (quantitative) of 5-(3-chlorophenyl)-α-(1-methyl-1H-imidazol-5-yl)-α-(4-methylphenyl)-tetrazolo[1,5-a]quinazoline-7-methanol (intermediate 25), mp. 200° C.

i) A mixture of intermediate 25 (0.0083 mol) in thionyl chloride (80 ml) was stirred at 60° C. for 3 hours, then cooled and the solvent was evaporated. The residue was taken up in DCM. The solvent was evaporated, yielding 7-[chloro(1-methyl-1H-imidazol-5-yl)(4-methylphenyl)methyl]-5-(3-chlorophenyl)-tetrazolo[1,5-a]quinazoline. hydrochloride (1:1) (intermediate 26). This product was used directly in the next reaction step.

j) A mixture of intermediate 26 (0.0083 mol) in THF (80 ml) was cooled to 5° C. under N$_2$ flow. NH$_3$/iPrOH (80 ml) was added dropwise. The mixture was stirred at 5° C. for 1 hours, then brought to room temperature. The mixture was stirred at room temperature overnight, poured out into ice water and extracted with DCM. The organic layer was separated, washed with water, dried (MgSO$_4$), filtered and the solvent was evaporated. The residue was purified by column chromatography over silica gel (15-40 μm) (eluent: DCM/MeOH/NH$_4$OH 96/4/0.2). The pure fractions were collected and the solvent was evaporated. The residue was crystallized from CH$_3$CN. The precipitate was filtered off and dried, yielding 1.37 g (33%) of 5-(3-chlorophenyl)-α-(1-methyl-1H-imidazol-5-yl)-α-(4-methylphenyl)-tetrazolo[1,5-a]quinazoline-7-methanamine hydrate (1:1) (intermediate 27), mp. 150° C.

k) Sodium hydroborate (0.0005 mol) was added portionwise at room temperature to a mixture of intermediate 27 (0.0005 mol) in methanol (2.5 ml). The mixture was stirred at room temperature for 2 hours and poured out into ice water. DCM was added. The mixture was extracted with DCM. The organic layer was separated, washed with water, dried (MgSO$_4$), filtered and the solvent was evaporated. The residue was purified by column chromatography over kromasil® (5 μm) (eluent: DCM/MeOH/Et$_3$N 97/3/0.3). The pure fractions were collected and the solvent was evaporated. The residue (0.1 g, 40%) was taken up in diethyl ether and dried in a vacuo, yielding 0.07 g (28%) of 5-(3-chlorophenyl)-4,5-dihydro-α-(1-methyl-1H-imidazol-5-yl)-α-(4-methylphenyl)-tetrazolo[1,5-a]quinazoline-7-methanamine (intermediate 28), mp. 140° C.

EXAMPLE A4

Preparation of

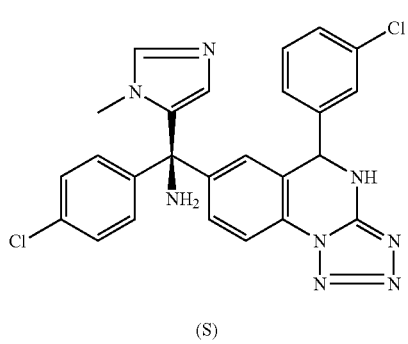

intermediate 29

(S)

Sodium tetrahydroborate (0.0011 mol) was added at 5° C. to a mixture of (+)-5-(3-chlorophenyl)-α-(4-chlorophenyl)-α-(1-methyl-1H-imidazol-5-yl)-tetrazolo[1,5-a]quinazoline-7-methanamine (described in International Application WO01/98302) (0.001 mol) in THF (5 ml) under N$_2$ flow. The mixture was stirred for 2 hours, poured out into ice water and extracted with DCM. The organic layer was separated, dried (MgSO$_4$), filtered, and the solvent was evaporated. The residue was purified by column chromatography over silica gel (35-70 μm) (eluent: DCM/MeOH/NH$_4$OH 95/5/0.1). The pure fractions were collected and the solvent was evaporated. The residue was crystallized from diethyl ether. The precipitate was filtered off and dried, yielding 0.13 g (26%) of intermediate 29 (S), mp. 180° C.

EXAMPLE A5 a) Preparation of

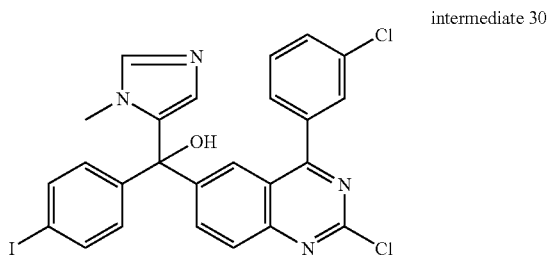

intermediate 30

1-methyl-1H-imidazole (0.0142 mol) was added at −70° C. to THF (14 ml) under N$_2$ flow. BuLi (0.0142 mol) was added dropwise. The mixture was kept for 15 minutes. Chlorotriethyl-silane (0.0146 mol) was added slowly. The mixture was kept for 15 minutes. BuLi (0.0126 mol) was added dropwise. The mixture was kept for 15 minutes. A solution of [2-chloro-4-(3-chlorophenyl)-6-quinazolinyl](4-iodophenyl)-methanone (described in International patent application WO02/24683) (0.0081 mol) in THF (16 ml) was added. The mixture was kept for 1 hour, poured out into water and extracted with DCM. The organic layer was separated, dried (MgSO$_4$), filtered, and the solvent was evaporated till dryness. The residue (7.4 g) was purified by column chromatography over silica gel (15-40 μm) (eluent: DCM/MeOH/NH$_4$OH; 97/3/0.1). The pure fractions were collected and the solvent was evaporated, yielding 2.3 g (48%) of intermediate 30.

b) Preparation of

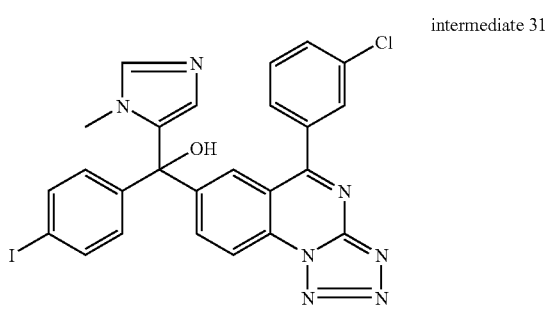

intermediate 31

A mixture of intermediate 30 (0.0039 mol) and sodium azide (0.0117 mol) in in DMF (20 ml) was stirred at 140° C. for 1 hour then cooled and poured out into ice water. The precipitate was filtered, washed with water several times and taken up in DCM. The organic layer was separated, dried (MgSO₄), filtered, and the solvent was evaporated till dryness. The residue was crystallized from acetonitrile. The precipitate was filtered off and dried, yielding 1.8 g (78%) of intermediate 31, mp. >260° C.

c) Preparation of

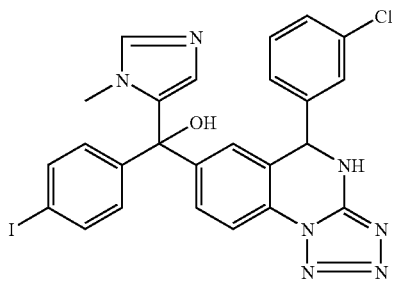

intermediate 32

Sodium hydroborate (0.002 mol) was added portionwise at room temperature to a solution of intermediate 31 (0.002 mol) in MeOH (12 ml). The mixture was stirred at room temperature for 2 hours. Ice and water were added. The precipitate was filtered off and dried. EtOAc was added to the filtrate. The mixture was extracted with DCM. The organic layer was separated, dried (MgSO₄), filtered, and the solvent was evaporated, yielding 0.116 g (79%) of intermediate 32.

EXAMPLE A6 a) Preparation of

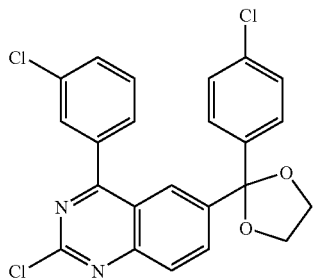

intermediate 33

A mixture of 4-(3-chlorophenyl)-6-[2-(4-chlorophenyl)-1,3-dioxolan-2-yl]-2(1H)-quinazolinone (described in International Application WO98/49157) (0.056 mol) in phosphoryl chloride (120 ml) was stirred at 110° C. for 1 hour, then cooled and the solvent was evaporated till dryness. The residue was taken up in DCM. The organic layer was poured out into diluted NH₄OH cooled with ice and extracted with DCM. The organic layer was separated, dried (MgSO₄), filtered, and the solvent was evaporated. The residue (27.9 g) was purified by column chromatography over silica gel (15-35 μm) (eluent: DCM/cyclohexane 80/20). The pure fractions were collected and the solvent was evaporated. The residue (14 g) was purified by column chromatography over silica gel (15-35 μm) (eluent: cyclohexane/EtOAc 80/20). The pure fractions were collected and the solvent was evaporated, yielding 11 g (42%) of intermediate 33, mp. 112° C.

b) Preparation of

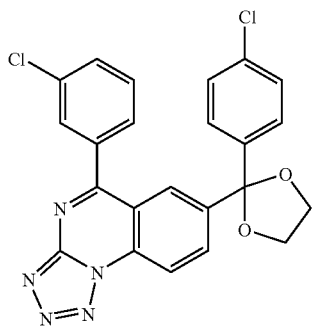

intermediate 34

Sodium azide (0.0108 mol) was added at room temperature to a mixture of intermediate 33 (0.01 mol) in DMA (50 ml). The mixture was stirred at room temperature for 48 hours. Water was added. The precipitate was filtered, washed with water and dried, yielding 5.9 g (>100%) of intermediate 34. This product was used directly in the next reaction step.

c) Preparation of

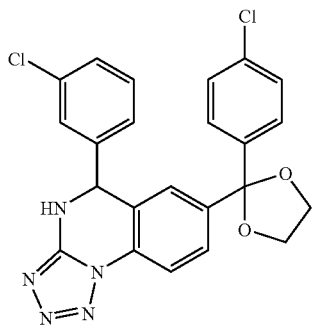

intermediate 35

Sodium hydroborate (0.01 mol) was added portionwise at 5° C. to a mixture of intermediate 34 (0.01 mol) in MeOH (75 ml) under N₂ flow. The mixture was stirred at room temperature for 2 hours. Water was added. The precipitate was filtered, washed with DIPE and dried. Part (0.58 g) of the residue (5.8 g) was crystallized from DCM/MeOH. The precipitate was filtered, washed with diethyl ether and dried, yielding 0.272 g (58%) of intermediate 35, mp. 190° C.

d) Preparation of

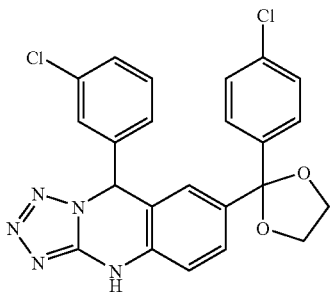

intermediate 36

A mixture of intermediate 35 (0.009 mol) in toluene (20 ml) and dioxane (25 ml) was stirred at 120° C. for 2 hours. The solvent was evaporated till dryness, yielding 4.4 g (105%) of intermediate 36.

e) Preparation of intermediate 37

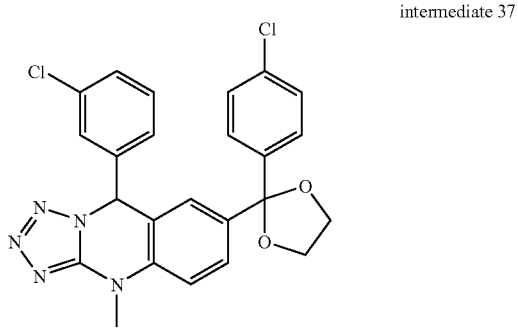

Sodium hydride 60% in oil (0.0005 mol) was added at room temperature to a mixture of intermediate 36 (0.0005 mol) in THF (3 ml) under $N_2$ flow. The mixture was stirred at room temperature for 15 minutes. Iodomethane (0.0005 mol) was added. The mixture was stirred for 2 hours. Water was added. The mixture was extracted with DCM. The organic layer was separated, dried (MgSO$_4$), filtered, and the solvent was evaporated. This fraction (0.15 g) was crystallized from DCM/MeOH/DIPE. The precipitate was filtered off and dried, yielding 0.137 g (57%) of intermediate 37, mp. 200° C.

f) Preparation of intermediate 38

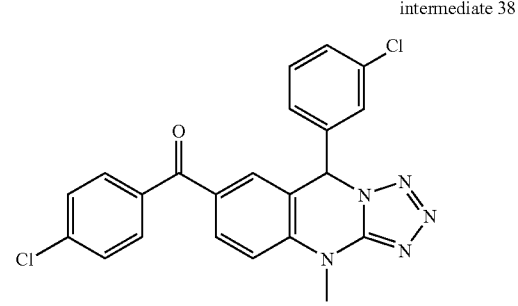

A mixture of intermediated (0.008 mol) in HCl 3N (35 ml) and MeOH (45 ml) was stirred at 60° C. for 5 hours, poured out into ice water and neutralized with NH$_4$OH. The precipitate was filtered off and dried. The residue (3.144 g) was crystallized from DCM/DIPE. The precipitate was filtered off and dried, yielding 2.57 g (74%) of intermediate 38, mp. 234° C.

EXAMPLE A7

Preparation of intermediate 39

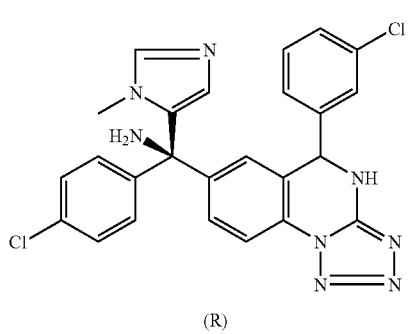

Sodium hydroborate (0.001 mol) was added at room temperature to a mixture of intermediate (−)-5-(3-chlorophenyl)-α-(4-chlorophenyl)-α-(1-methyl-1H-imidazol-5-yl)tetrazolo[1,5-a]quinazoline-7-methanamine (described in International Application WO01/98302) (0.001 mol) in THF (5 ml) under $N_2$ flow. The mixture was stirred at room temperature for 5 hours. Water was added. The mixture was extracted with DCM. The organic layer was separated, dried (MgSO$_4$), filtered, and the solvent was evaporated, yielding 0.5 g of intermediate 39 (R).

B. Preparation of the Final Compounds

EXAMPLE B1

A mixture of (±)-5-(3-chlorophenyl)-α-(4-chlorophenyl)-4,5-dihydro-α-(1-methyl-1H-imidazol-5-yl)tetrazolo[1,5-a]quinazoline-7-methanol described in International application WO00/39082 (0.0013 mol) in toluene (15 ml) was stirred at 120° C. for 6 hours, then cooled to room temperature and the solvent was evaporated till dryness. The residue was crystallized from DCM/MeOH/DIPE. The precipitate was filtered off and dried, yielding 0.19 g (27%) of 9-(3-chlorophenyl)-α-(4-chlorophenyl)-4,9-dihydro-α-(1-methyl-1H-imidazol-5-yl)-tetrazolo[5,1-b]quinazoline-7-methanol (compound 1), mp. >260° C.

EXAMPLE B2

A mixture of intermediate 9 (0.0014 mol) in toluene (10 ml) was stirred and refluxed for 48 hours, then brought to room temperature and the solvent was evaporated till dryness. The residue was taken up in DCM. The solvent was evaporated till dryness. The residue was purified by column chromatography over kromasil® (10 μm) (eluent: DCM/MeOH/Et$_3$N 95/5/0.1). The pure fractions were collected and the solvent was evaporated. The residue (0.4 g, 57%) was washed with diethyl ether. The precipitate was filtered off and dried under a vacuo, yielding 0.35 g (50%) of 9-(3-chlorophenyl)-α-(4-fluorophenyl)-4,9-dihydro-α-(1-methyl-1H-imidazol-5-yl)-tetrazolo[5,1-b]quinazoline-7-methanol (compound 2), mp. 180° C.

EXAMPLE B3

A mixture of intermediate 17 (0.0006 mol) in toluene (10 ml) was stirred and refluxed for 5 hours, then brought to room temperature and the solvent, was evaporated till dryness. The residue was taken up in DCM. The solvent was evaporated till dryness. The residue was purified by column chromatography over kromasil® (10 μm) (eluent: DCM/MeOH/Et$_3$N 95/5/0.5). The pure fractions were collected and the solvent was evaporated. The residue (0.12 g, 40%) was taken up in DCM. The solvent was evaporated till dryness, yielding 0.08 g (27%) of 9-(3-chlorophenyl)-4,9-dihydro-α-(4-methoxyphenyl)-α-(1-methyl-1H-imidazol-5-yl)-tetrazolo[5,1-b]quinazoline-7-methanol (compound 3).

EXAMPLE B4

A mixture of intermediate 28 (0.0001 mol) in toluene (1 ml) was stirred at 120° C. for 6 hours, then brought to room temperature and the solvent was evaporated till dryness. The residue was taken up in DCM. The solvent was evaporated till dryness. The residue was purified by column chromatography over kromasil® (10 μm) (eluent: DCM/MeOH 96/4). Two fractions were collected and the solvent was evaporated, yielding 0.012 g (24%) of 9-(3-chlorophenyl)-4,9-dihydro-α-(1-methyl-1H-imidazol-5-yl)-α-(4-methylphenyl)-tetrazolo[5,1-b]quinazoline-7-methanamine (diastereoisomer (A)) (compound 4) and 0.01 g (20%) of 9-(3-chlorophenyl)-4,9-dihydro-α-(1-methyl-1H-imidazol-5-yl)-α-(4-methylphenyl)-tetrazolo[5,1-b]quinazoline-7-methanamine (diastereoisomer (B)) (compound 5).

EXAMPLE B5

Preparation of

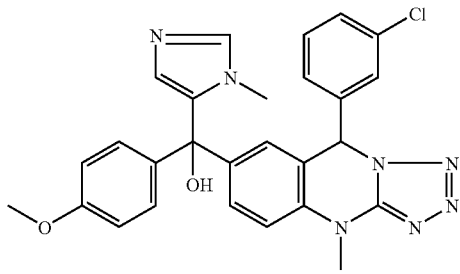

mixture of diastereoisomer (A/B) (80/20)
is compound 6

Sodium hydride (0.0005 mol) was added at room temperature to a mixture of compound 3 (0.0005 mol) in THF (3 ml) under N₂ flow. The mixture was stirred at room temperature for 30 minutes. Iodomethane (0.0005 mol) was added. The mixture was stirred at room temperature for 20 hours. Water was added. The mixture was extracted with DCM. The organic layer was separated, dried (MgSO₄), filtered, and the solvent was evaporated. The residue (0.33 g) was purified by column chromatography over kromasil® (10 μm) (eluent: DCM/MeOH/NH₄OH 92/8/0.2). The pure fractions were collected and the solvent was evaporated. The residue (0.083 g) was taken up in diethyl ether. The precipitate was filtered off and dried, yielding 0.06 g (23%) (mixture of diastereoisomers (A/B) (80/20)) of compound 6, mp. 149° C.

EXAMPLE B6

Preparation of

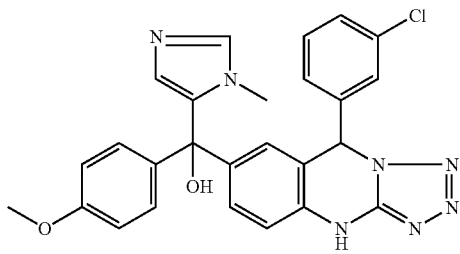

diastereoisomer (A)
is compound 7

-continued

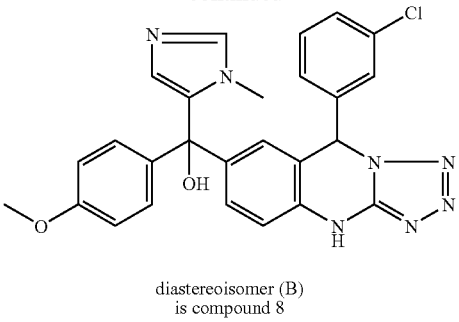

diastereoisomer (B)
is compound 8

A mixture of intermediate 17 (0.0043 mol) in toluene (12.5 ml) and dioxane (12.5 ml) was stirred at 120° C. for 2 hours. The solvent was evaporated till dryness. The residue was taken up in DCM/MeOH. The solvent was evaporated till dryness. The residue (2.05 g, 94%) was crystallized from DCM/MeOH/CH₃CN. The precipitate was filtered, washed with diethyl ether and dried, yielding 0.8 g (36%) of compound 7 (diastereoisomer (A)), mp. >260° C. The mother layer was evaporated. Part (0.3 g) of the residue (1.3 g) was purified by column chromatography over silica gel (35-40 μm) (eluent: DCM/iPrOH/NH₄OH 90/10/0.1). The pure fractions were collected and the solvent was evaporated. The residue (0.06 g) was crystallized from DCM/diethyl ether. The precipitate was filtered off and dried, yielding 0.037 g (7%) of compound 8 (diastereoisomer (B)), mp. 176° C.

EXAMPLE B7

Preparation of compound 9

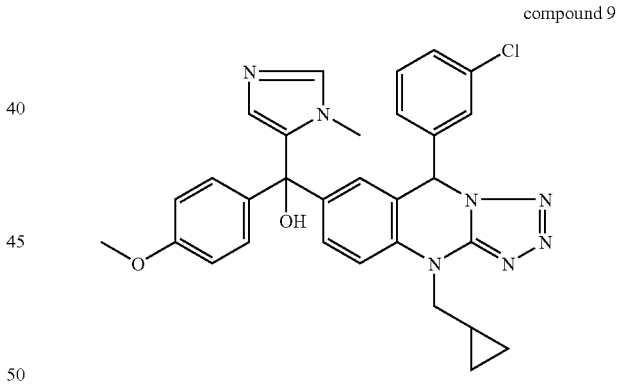

Sodium hydride (0.0012 mol) was added at room temperature to a mixture of compound 7 (diastereoisomer (A)) (0.0005 mol) in THF (3 ml) under N₂ flow. The mixture was stirred at room temperature for 15 minutes. (bromomethyl)-cyclopropane (0.0012 mol) was added. The mixture was stirred at room temperature for 2 hours, then at 40° C. for 1 hour, then at 60° C. for 2 hours. DMF (1 ml) was added. The mixture was stirred at 60° C. for 1 hour. Water was added. The mixture was extracted with EtOAc. The organic layer was separated, dried (MgSO₄), filtered; and the solvent was evaporated. The residue (0.38 g) was purified by column chromatography over kromasil® (10 μm) (eluent: DCM/MeOH 97/3). The pure fractions were collected and the solvent was evaporated). This residue (0.075 g, 27%) was crystallized from DIPE. The precipitate was filtered off and dried, yielding 0.065 g of compound 9, mp. 121° C.

EXAMPLE B8

Preparation of

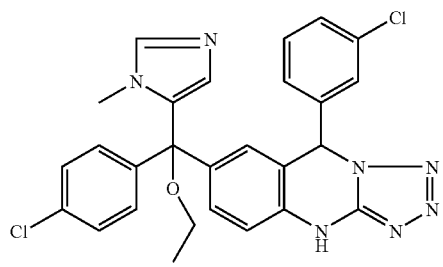

compound 10

Thionyl chloride (0.1 ml) was added at room temperature to a mixture of compound 1 (0.0002 mol) in EtOH (2 ml). The mixture was stirred at room temperature for 2 hours. Water was added. The mixture was taken up in DCM. The organic layer was separated, dried ($MgSO_4$), filtered, and the solvent was evaporated. The residue (0.15 g) was purified by column chromatography over kromasil® (10 µm) (eluent: DCM/MeOH 98/2). The pure fractions were collected and the solvent was evaporated. The residue (0.03 g) was taken up in DCM and evaporated till dryness, yielding 0.023 g (17%) of compound 10.

EXAMPLE B9

Preparation of

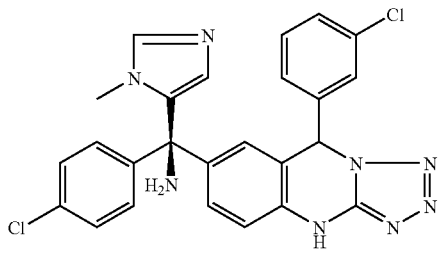

diastereoisomer (S) (B)
is compound 11

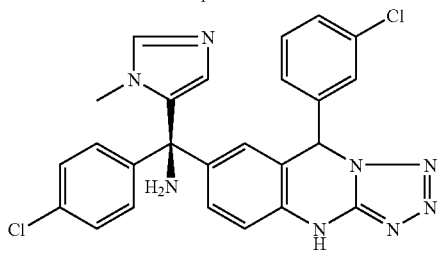

diastereoisomer (S) (A)
is compound 12

A mixture of intermediate 29 (S) (0.002 mol) in toluene (5 ml) and dioxane (7.5 ml) was stirred at 110° C. for 2 hours, then cooled to room temperature. The solvent was evaporated till dryness. The residue (1 g) was purified by column chromatography over silica gel (15-40 µm) (eluent: DCM/MeOH/$NH_4OH$ 93/7/0.1 to 93/7/0.5). Two fractions were collected and the solvent was evaporated, yielding 0.24 g (diastereoisomer (S) (B)) (24%) F1 and 0.26 g (diastereoisomer (S) (A)) (26%) F2. F2 was crystallized from DCM/$CH_3CN$. The precipitate was filtered off and dried, yielding 0.159 g (16%) of compound 12 (diastereoisomer (S) (A)), mp. 162° C. F1 was crystallized from DCM/MeOH/$CH_3CN$. The precipitate was filtered off and dried, yielding 0.157 g (16%) of compound 11 (diastereoisomer (S) (B)), mp. 242° C.

EXAMPLE B10

Preparation of

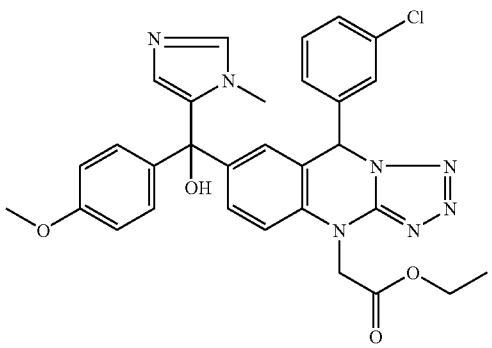

mixture of diastereoisomers (A/B) (75/25)
is compound 13

Sodium hydride (0.0006 mol) was added at room temperature to a mixture of compound 7 (diastereoisomer (A)) (0.0005 mol) in DMF (3 ml) under $N_2$ flow. The mixture was stirred at room temperature for 30 minutes. Chloro-acetic acid, ethyl ester (0.0006 mol) was added. The mixture was stirred at room temperature for 1 hour. Water (10 ml) was added. The mixture was stirred at room temperature for 15 minutes. The precipitate was filtered, washed with DIPE and dried. The residue was dissolved in DCM. The organic layer was dried ($MgSO_4$), filtered, and the solvent was evaporated. The residue (0.22 g) was purified by column chromatography over kromasil® (10 µm) (eluent: DCM/MeOH 97/3). The pure fractions were collected and the solvent was evaporated. The residue (0.2 g, 68%) was crystallized from DCM/$CH_3CN$/DIPE. The precipitate was filtered off and dried, yielding 0.105 g of compound 13 (mixture of diastereoisomers (A/B) (75/25)), mp. 126° C.

EXAMPLE B11

Preparation of

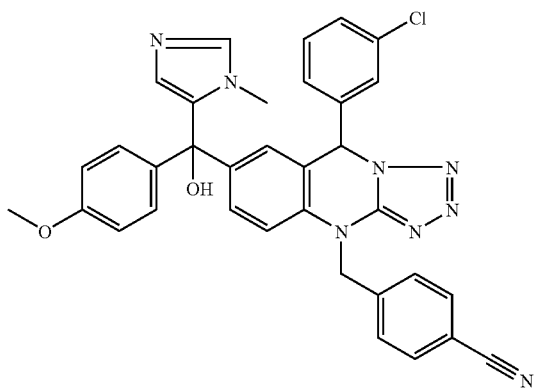

mixture of diastereoisomers (A/B) (65/35)
is compound 14

Sodium hydride (0.0006 mol) was added at room temperature to a mixture of compound 7 (diastereoisomer (A)) (0.0005 mol) in DMF (3 ml) under N₂ flow. The mixture was stirred at room temperature for 1 hour. Water was added. The precipitate was filtered, washed several times with DIPE and dried. The residue (0.3 g) was purified by column chromatography over kromasil® (10 μm) (eluent: DCM/MeOH 97/3). The pure fractions were collected and the solvent was evaporated. The residue 0.2 g) was crystallized from CH₃CN/DIPE. The precipitate was filtered off and dried, yielding 0.12 g of compound 14 (mixture of diastereoisomers (A/B) (65/35)), mp. 164° C.

EXAMPLE B12

Preparation of

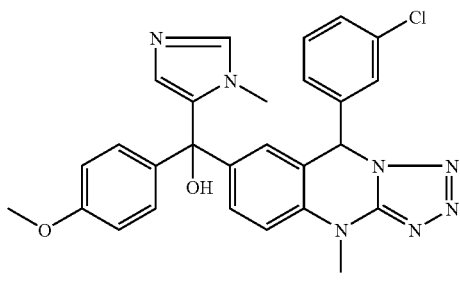

mixture of diastereoisomers (A/B) (50/50)
is compound 15

Sodium hydride (0.0024 mol) was added portionwise at room temperature to a mixture of compound 3 (0.0021 mol) in DMF (10 ml) under N₂ flow. The mixture was stirred at room temperature for 1 hour. Iodomethane (0.0024 mol) was added. The mixture was stirred at room temperature for 2 hours and 30 minutes. Water (20 ml) was added. The precipitate was filtered and taken up in DCM. The organic layer was separated, dried (MgSO₄), filtered and the solvent was evaporated. The residue (1 g) was purified by column chromatography over silica gel (15-40 μm) (eluent: DCM/MeOH/NH4OH 95/5/0.1). The pure fractions were collected and the solvent was evaporated. The residue (0.74 g 71%) was crystallized from DCM/CH₃CN/DIPE. The precipitate was filtered off and dried, yielding 0.166 g of compound 15 (mixture of diastereoisomers (A/B) (50/50)), mp. 144° C.

EXAMPLE B13

Preparation of

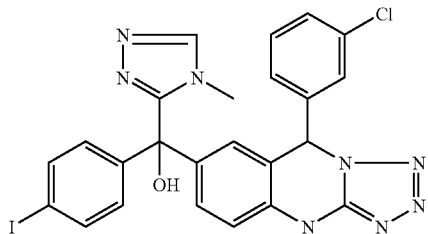

mixture of diastereoisomers (A/B) (77/23)
is compound 16

-continued

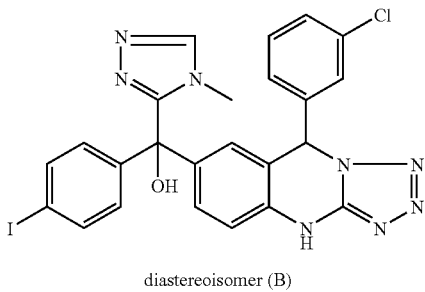

diastereoisomer (B)
is compound 17

A mixture of 5-(3-chlorophenyl)-1,5-dihydro-∝-(4-iodophenyl)-∝-(4-methyl-4H-1,2,4-triazol-3-yl)-tetrazolo[1,5-a]quinazoline-7-methanol (described in International Application WO02/24683) (0.0012 mol) in toluene (3.5 ml) and dioxane (5.25 ml) was stirred at 110° C. for 2 hours, then cooled to room temperature and the solvent was evaporated till dryness. The residue (0.731 g) was crystallized from DCM/MeOH/DIPE. The precipitate was filtered off and dried, yielding 0.367 g of compound 16 (mixture of diastereoisomers 77/23), mp. 226° C. The filtrate was evaporated. The residue (0.34 g) was purified by column chromatography over silica gel (40 μm) (eluent: toluene/iPrOH/NH₄OH 85/15/1 to 80/20/1). The pure fractions were collected and the solvent was evaporated. The residue (0.07 g) was crystallized from DCM/MeOH/DIPE. The precipitate was filtered off and dried, yielding 0.05 g (7%) of compound 17 (diastereoisomer (B)), mp. 195° C.

EXAMPLE B14

Preparation of

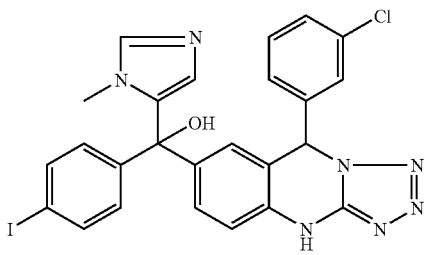

mixture of diastereoisomers (A/B) (80/20)
is compound 18

A mixture of intermediate 32 (0.0015 mol) in toluene (4.6 ml) and dioxane (6.9 ml) was stirred at 110° C. for 2 hours, then cooled to room temperature and the solvent was evaporated till dryness. The residue (1.32 g) was crystallized from DCM/MeOH/DIPE. The precipitate was filtered off and dried, yielding 0.85 g (90%) of compound 18, (mixture of diastereoisomers (A/B) (80/20)), mp. 225° C.

EXAMPLE B15

Preparation of

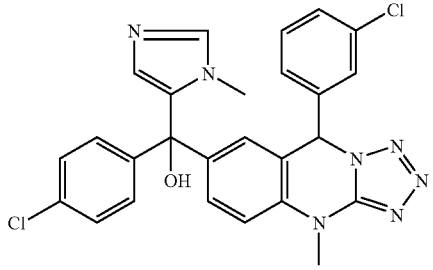

mixture of diastereoisomers (A/B) (50/50)
is compound 19

BuLi 1.6M in hexane (0.0095 mol, 5.95 ml) was added at −78° C. to a solution of 1-methyl-1H-imidazole (0.0095 mol) in THF (8 ml) under $N_2$ flow. The mixture was stirred at −78° C. for 15 minutes. chlorotriethyl-silane (0.0097 mol) was added slowly. The mixture was stirred at −78° C. for 15 minutes. BuLi 1.6M in hexane (0.0084 mol, 5.27 ml) was added. The mixture was stirred at −78° C. for 15 minutes. A solution of intermediate 38 (0.0054 mol) in THF (9 ml) was added dropwise. The mixture was stirred at −78° C. for 3 hours, then brought to 0° C. Water and ice were added. The precipitate was filtered off and dried. DCM was added to the filtrate. The organic layer was separated, dried (MgSO$_4$), filtered, and the solvent was evaporated. The residue (2.48 g) was purified by column chromatography over silica gel (15-40 μm) (eluent: DCM/MeOH/NH$_4$OH 98/2/0.1 to 94/6/0.5). The pure fractions were collected and the solvent was evaporated. The residue (0.1 g) was crystallized from DCM/DIPE. The precipitate was filtered off and dried, yielding 0.031 g (3%) of compound 19 (mixture of diastereoisomers (A/B) (50/50)).

EXAMPLE B16

Preparation of

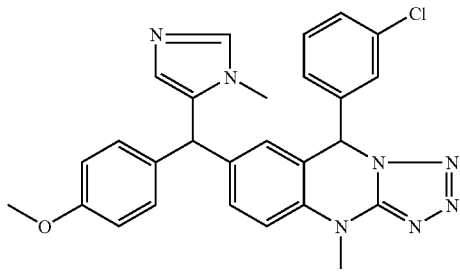

mixture of diastereoisomers (A/B) (60/40)
is compound 20

A mixture of compound 15 (mixture of diastereoisomers (A/B) (50/50)) (0.0007 mol) in formamide (2 ml) and acetic acid (4 ml) was stirred at 160° C. for 3 hours, poured out into ice/NH$_4$OH and extracted with DCM. The organic layer was separated, dried (MgSO$_4$), filtered, and the solvent was evaporated. The residue (0.55 g) was purified by column chromatography over silica gel (40 μm) (eluent: DCM/MeOH 97/3). The pure fractions were collected and the solvent was evaporated, yielding and 0.085 g (23%) of compound 20 (mixture of diastereoisomers (A/B) (60/40)), mp. 108° C.

EXAMPLE B17

Preparation of

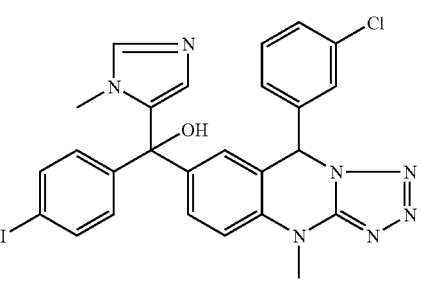

mixture of diastereoisomers (A/B) (50/50)
is compound 21

Sodium hydride 60% in oil (0.0015 mol) was added portionwise at room temperature to a mixture of compound 18 (mixture of diastereoisomers (A/B) (80/20)) (0.0013 mol) in DMF (8 ml) under $N_2$ flow. The mixture was stirred at room temperature for 1 hour. Iodomethane (0.0015 mol) was added. The mixture was stirred at room temperature for 1 hour. Water was added. The precipitate was filtered off and dried. The residue (0.874 g) was purified by column chromatography over silica gel (40 μm) (eluent: DCM/MeOH/NH$_4$OH 97/3/0.1). The pure fractions were collected and the solvent was evaporated, yielding: 0.479 g (60%) of compound (R318150) A sample was crystallized from DCM/DIPE. The precipitate was filtered off and dried. Yielding: 0.07 g of compound 21 (mixture of diastereoisomers (A/B) (50/50)), mp. 228° C.

EXAMPLE B18

Preparation of

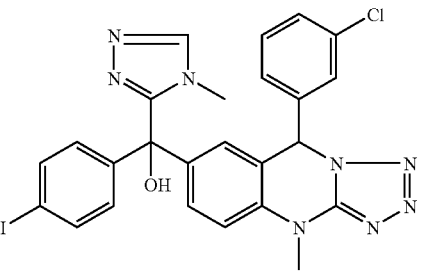

mixture of diastereoisomers (A/B) (87/13)
is compound 22

Sodium hydride 60% in oil (0.0003 mol) was added portionwise at room temperature to a mixture of compound 16

(mixture of diastereoisomers (A/B) (77/23)) (0.0002 mol) in DMF (1.5 ml) under N₂ flow. The mixture was stirred at room temperature for 1 hour. Iodomethane (0.0002 mol) was added. The mixture was stirred at room temperature for 1 hour and 30 minutes. Water was added. The precipitate was filtered. EtOAc was added to the filtrate. The organic layer was separated, dried (MgSO₄), filtered, and the solvent was evaporated. The residue (0.08 g) was purified by column chromatography over silica gel (40 µm) (eluent: DCM/MeOH/NH₄OH 95/5/0.1). The pure fractions were collected and the solvent was evaporated. The residue (0.071 g) was crystallized from CH₃CN/DCM. The precipitate was filtered off and dried, yielding 0.054 g of compound 22 (mixture of diastereoisomers (A/B) (87/13)), mp. 81° C.

EXAMPLE B19

Preparation of

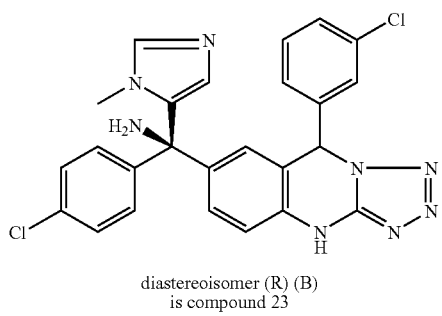

diastereoisomer (R) (B)
is compound 23

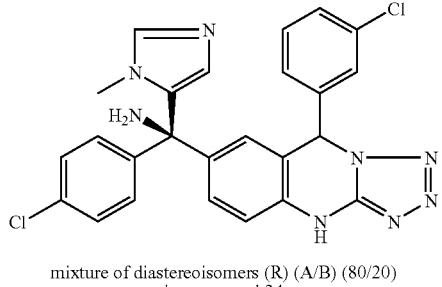

mixture of diastereoisomers (R) (A/B) (80/20)
is compound 24

A mixture of intermediate 39 (R) (0.001 mol) in toluene (3 ml) and dioxane (3 ml) was stirred at 110° C. for 3 hours, then cooled to room temperature and the solvent was evaporated till dryness. The residue (0.6 g) was purified by column chromatography over kromasil® (10 µm) (eluent: DCM/MeOH/NH₄OH 93/7/0.5). The pure fractions were collected and the solvent was evaporated. This fraction (0.29 g) was crystallized from DCM/DIPE. The precipitate was filtered off and dried, yielding 0.1 g (20%) of compound 23 (diastereoisomer (R) (B)), mp. >250° C. The filtrate was evaporated. The residue (0.18 g) was taken up in diethyl ether. The precipitate was filtered off and dried, yielding 0.158 g (31%) of compound 24 (mixture of diastereoisomers (R) (A/B) (80/20)), mp. 183° C.

EXAMPLE B20

Preparation of

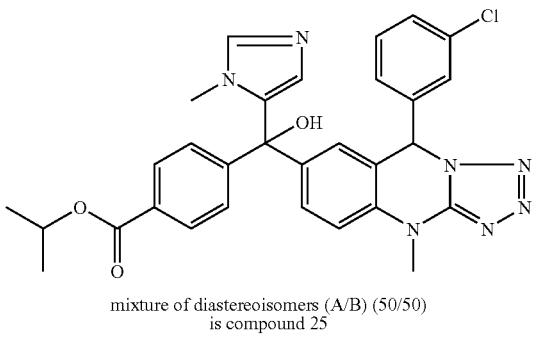

mixture of diastereoisomers (A/B) (50/50)
is compound 25

A mixture of compound 21 (mixture of diastereoisomers (A/B) (50/50)) (0.0006 mol), acetic acid palladium(2+) salt (0.00007 mol), triphenyl-phosphine (0.001 mol) and potassium carbonate (0.0013 mol) in DMF (4 ml) and 2-propanol (4 ml) was stirred at 90° C. for 18 hours under a 5 bar pressure of CO, then cooled to room temperature and filtered over celite. Celite was washed with EtOAc, then with water. The organic layer was separated, dried (MgSO₄), filtered, and the solvent was evaporated. The residue (0.94 g) was purified by column chromatography over silica gel (15-40 µm) (eluent: DCM/MeOH/NH₄OH 93/7/0.1). The pure fractions were collected and the solvent was evaporated. The residue (0.17 g, 43%) was crystallized from diethyl ether. The precipitate was filtered off and dried, yielding 0.089 g (22%) of compound 25 (mixture of diastereoisomers (A/B) (50/50)), mp. 165° C.

Table F-1 lists the compounds that were prepared according to one of the above EXAMPLEs. The following abbreviations were used in the tables: Co.No. stands for Compound Number, Ex. [Bn°] refers to the same method as described in the Bn° examples. Some compounds have been characterized via melting point (mp.).

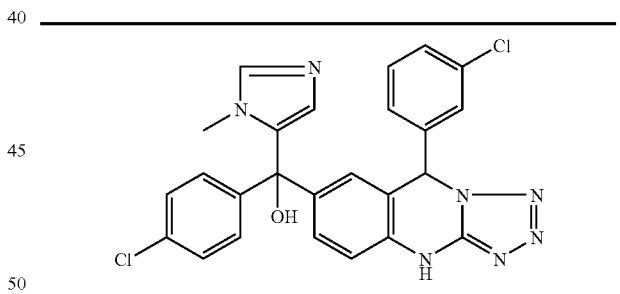

Co. No. 1; Ex. [B1]; mp > 260° C.

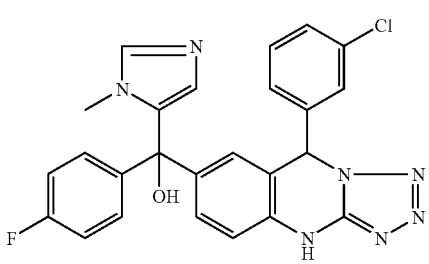

Co. No. 2; Ex. [B2]; mp 180° C.

-continued
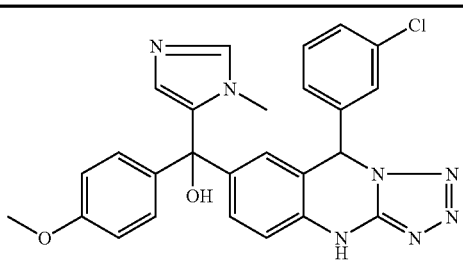
Co. No. 3; Ex. [B3]
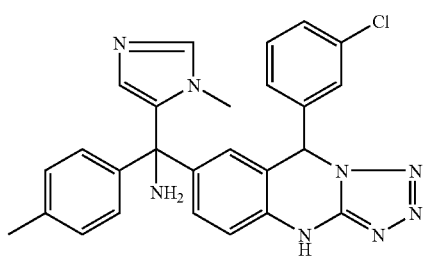
diastereoisomer (A); Co. No. 4; Ex. [B4]
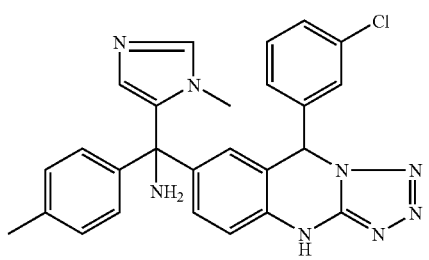
diastereoisomer (B); Co. No. 5; Ex. [B4]
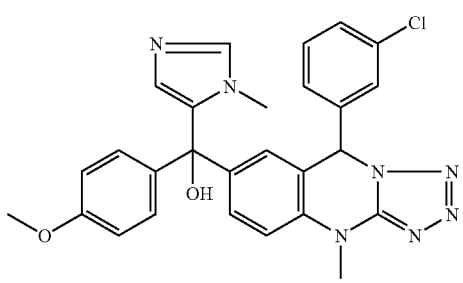
mixture of diastereoisomers (A/B) (80/20),
Co. No. 6; Ex. [B5] ; mp. 149° C.
-continued
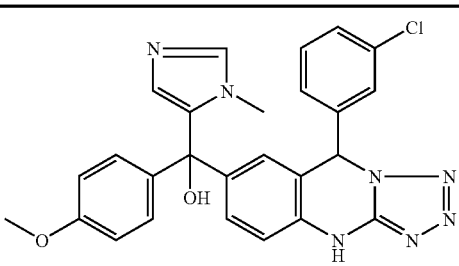
diastereoisomers (A); Co. No.7 Ex. [B6];
m.p. >260° C.
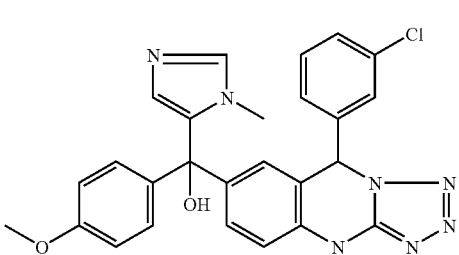
diastereoisomers (B); Co. No. 8; Ex. [B6];
mp. 176° C.
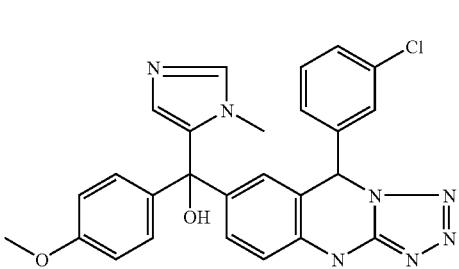
Co. No. 9; Ex. [B7];mp. 121° C.
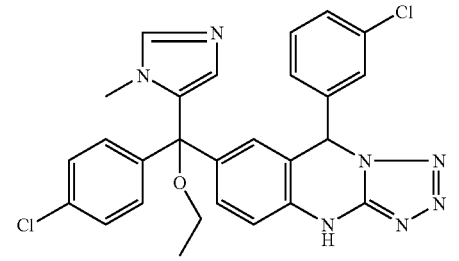
Co. No. 10; Ex. [B8];

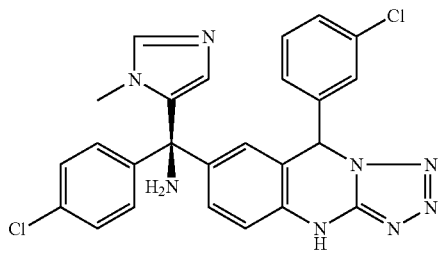
diastereoisomer (S) (B); Co. No. 11; Ex. [B9]; mp. 242° C.
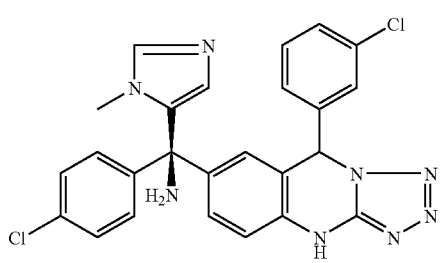
diastereoisomer (S) (A); Co. No. 12; Ex. [B9]; mp. 162° C.
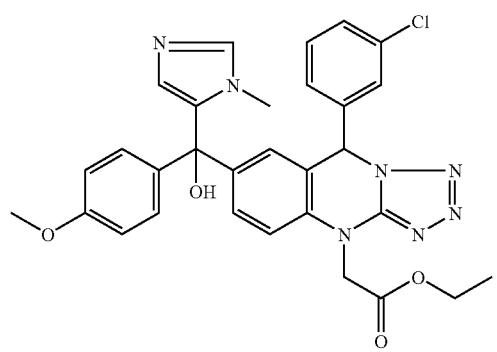
mixtures of diastereoisomers (A/B) (75/25); Co. No. 13; Ex. [B10]; mp. 126° C.
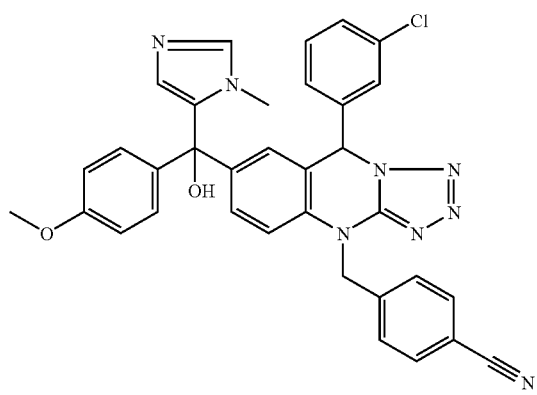
mixtures of diastereoisomers (A/B) (65/35); Co. No. 14; Ex. [B11]; mp. 164° C.
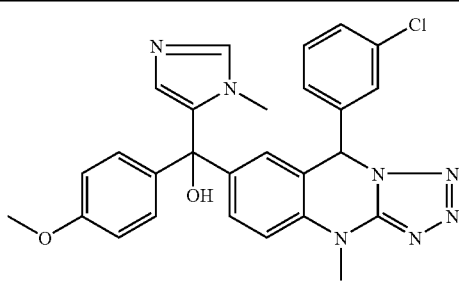
mixture of diastereoisomers (A/B) (50/50); Co. No. 15; Ex. [B12]; mp. 144° C.
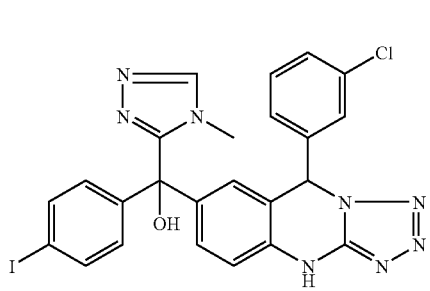
mixture of diastereoisomers (A/B) (73/23); Co. No. 16; Ex. [B13]; mp. 266° C.
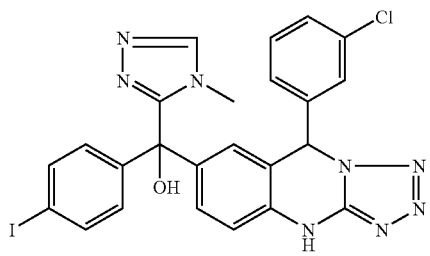
diastereoisomers (B); Co. No. 17; Ex. [B13]; mp. 195° C.
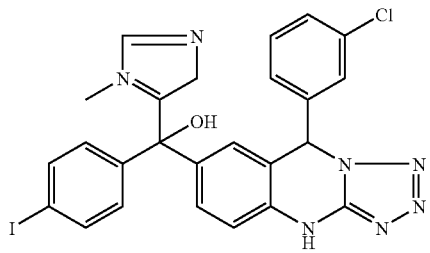
mixture of diastereoisomers (A/B) (80/20); Co. No. 18; Ex. [B14]; mp. 225° C.

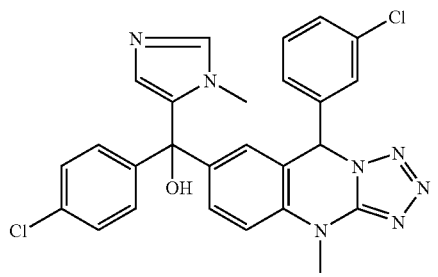

mixture of diastereoisomers (A/B) (50/50)
Co. No. 19; Ex. [B15]

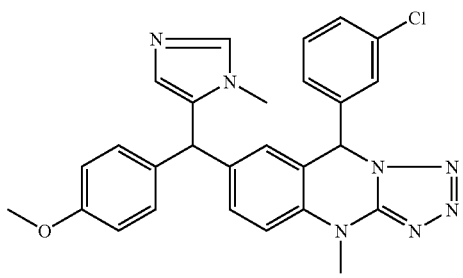

mixture of diastereoisomers (A/B)
(60/40); Co. No. 20; Ex. [B16]; mp.108° C.

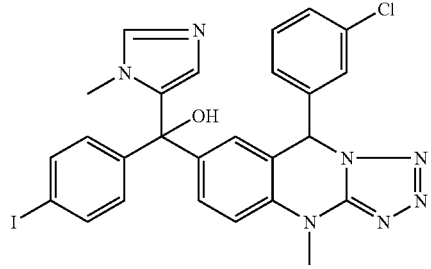

mixture of diastereoisomers (A/B) (50/50);
Co. No. 21; Ex. [B17]; mp. 228° C.

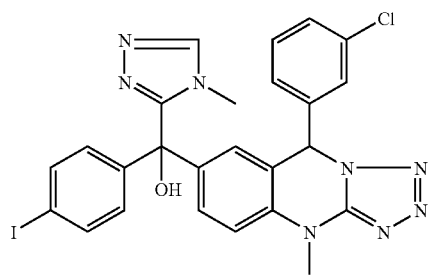

mixture of diastereoisomers (A/B)
(87/13); Co. No. 22; Ex. [B18]; mp. 181° C.

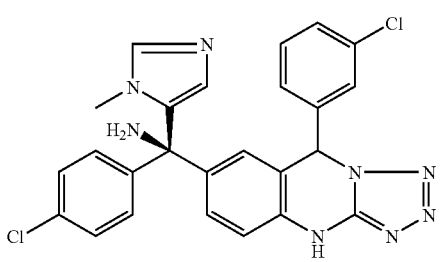

mixture of diastereoisomers (R) (A/B)
(80/20); Co. No. 24; Ex. [B19]

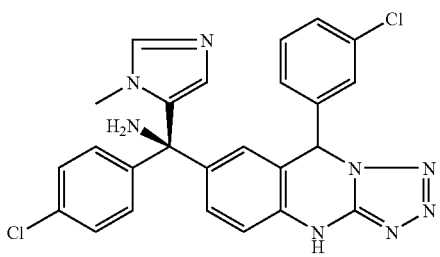

diastereoisomers (R) (B); Co. No. 23; Ex.
[B19]

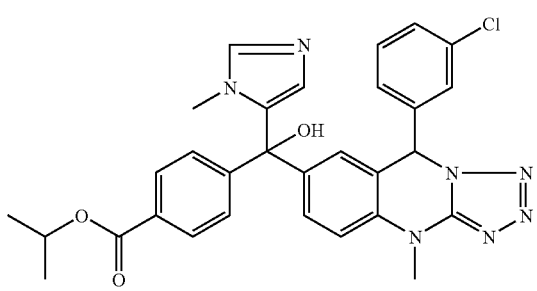

mixture of diastereoisomers (A/B) (50/50)
Co. No. 25; Ex. [B20]

C. Pharmacological Example

EXAMPLE C.1

In Vitro Assay for Inhibition of Farnesyl Protein Transferase

An in vitro assay for inhibition of farnesyl transferase was performed essentially as described in WO 98/40383, pages 33-34. Herein the effects of test compounds are expressed as $pIC_{50}$ (the negative log value of the $IC_{50}$-value) and as % of inhibition at $10^{-7}$ M (see Table F-2)

EXAMPLE C.2

Ras-Transformed Cell Phenotype Reversion Assay

The ras-transformed cell phenotype reversion assay can be performed essentially as described in WO 98/40383, pages 34-36.

TABLE F-2

Table F-2 lists the results of the compounds that were tested according to example C.1.

| Co. No. | Enzyme activity pIC50 | % of inhibition at $10^{-7}$ M |
|---|---|---|
| 1 | 7.596 | 81 |
| 2 | 8.753 | 96 |
| 3 | 7.632 | 80 |
| 4 | 7.461 | 74 |
| 5 | >9 | 99 |
| 6 | 7.851 | 90 |
| 7 | >7 | 64 |
| 8 | 7.906 | 88 |
| 9 | 7.686 | 82 |
| 10 | <7 | 43 |
| 11 | <7 | 46 |
| 12 | <7 | 42 |
| 13 | 7.596 | 80 |
| 14 | 7.731 | 74 |
| 15 | 7.78 | 88 |
| 16 | <7 | 45 |
| 17 | <7 | 42 |
| 18 | 7.524 | 76 |
| 19 | 8.013 | 92 |
| 20 | 8.036 | 91 |
| 21 | 7.718 | 78 |
| 22 | >7 | 57 |
| 23 | 8.595 | 98 |
| 24 | 7.933 | 88 |
| 25 | >7 | 66 |

D. Composition Example: Film-Coated Tablets

Preparation of Tablet Core

A mixture of 100 g of a compound of formula (I), 570 g lactose and 200 g starch is mixed well and thereafter humidified with a solution of 5 g sodium dodecyl sulfate and 10 g polyvinyl-pyrrolidone in about 200 ml of water. The wet powder mixture is sieved, dried and sieved again. Then there are added 100 g microcrystalline cellulose and 15 g hydrogenated vegetable oil. The whole is mixed well and compressed into tablets, giving 10.000 tablets, each comprising 10 mg of a compound of formula (I).

Coating

To a solution of 10 g methyl cellulose in 75 ml of denaturated ethanol there is added a solution of 5 g of ethyl cellulose in 150 ml of dichloromethane. Then there are added 75 ml of dichloromethane and 2.5 ml 1,2,3-propanetriol 10 g of polyethylene glycol is molten and dissolved in 75 ml of dichloromethane. The latter solution is added to the former and then there are added 2.5 g of magnesium octadecanoate, 5 g of polyvinyl-pyrrolidone and 30 ml of concentrated colour suspension and the whole is homogenated. The tablet cores are coated with the thus obtained mixture in a coating apparatus.

The invention claimed is:

1. A compound of formula (I):

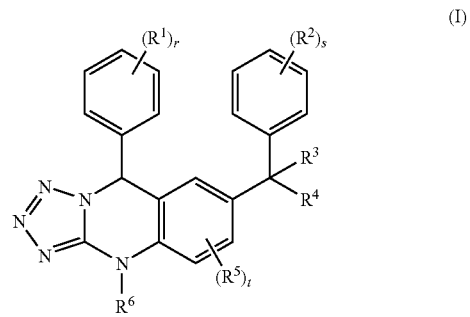

(I)

or a pharmaceutically acceptable salt or N-oxide or stereochemically isomeric form thereof, wherein r and s are each independently 0, 1, 2 or 3;

t is 0, 1, or 2;

each $R^1$ and $R^2$ are independently hydroxy, halo, cyano, nitro, $C_{1-6}$alkyl, —$(CR^{16}R^{17})_p$— $C_{3-10}$cycloalkyl, cyano$C_{1-6}$alkyl, hydroxy$C_{1-6}$alkyl, $C_{1-6}$alkyloxy$C_{1-6}$alkyl, hydroxycarbonyl$C_{1-6}$alkyl, $R^{20}SC_{1-6}$alkyl, trihalomethyl, aryl$C_{1-6}$alkyl, Het$^1C_{1-6}$alkyl, —$C_{1-6}$alkyl-$NR^{18}R^{19}$, —$C_{1-6}$alkyl$NR^{18}C_{1-6}$alkyl-$NR^{18}R^{19}$, —$C_{1-6}$alkyl$NR^{18}COC_{1-6}$alkyl, —$C_{1-6}$alkyl$NR^{18}COAlkAr^1$, —$C_{1-6}$alkyl$NR^{18}COAr^1$, $C_{1-6}$alkylsulphonylamino$C_{1-6}$alkyl, $C_{1-6}$alkyloxy, hydroxy$C_{1-6}$alkyloxy, $C_{1-6}$alkyloxy$C_{1-6}$alkyloxy, —$OC_{1-6}$alkyl-$NR^{18}R^{19}$, trihalomethoxy, aryl$C_{1-6}$alkyloxy, Het$^1C_{1-6}$alkyloxy, $C_{2-6}$alkenyl, cyano$C_{2-6}$alkenyl, —$C_{2-6}$alkenyl-$NR^{18}R^{19}$, hydroxycarbonyl$C_{2-6}$alkenyl, $C_{1-6}$alkyloxycarbonyl$C_{2-6}$alkenyl, $C_{2-6}$alkynyl, —CHO, $C_{1-6}$alkylcarbonyl, hydroxy$C_{1-6}$alkylcarbonyl, hydroxycarbonyl, $C_{1-6}$alkyloxycarbonyl, —$CONR^{18}R^{19}$, —$CONR^{18}$—$C_{1-6}$alkyl-$NR^{18}R^{19}$, —$CONR^{18}$—$C_{1-6}$alkyl-Het$^1$, —$CONR^{18}$—$C_{1-6}$alkyl-Ar$^1$, —$CONR^{18}$—O—$C_{1-6}$alkyl, —$CONR^{18}$—$C_{1-6}$alkenyl, —$NR^{18}R^{19}$, —$OC(O)R^{20}$, —$CR^{20}$=$NR^{21}$, —$CR^{20}$=N—$OR^{21}$, —$NR^{20}C(O)NR^{18}R^{19}$, —$NR^{20}SO_2R^{21}$, —$NR^{20}C(O)R^{21}$, —S—$R^{20}$, —S(O)—$R^{20}$, —$S(O)_2R^{20}$, —$SO_2NR^{20}R^{21}$, —$C(NR^{22}R^{23})$=$NR^{24}$, or a group of formula —CO-Z or —CO—NR$^y$-Z in which $R^y$ is hydrogen or $C_{1-4}$alkyl and Z is phenyl or a 5- or 6-membered heterocyclic ring containing one or more heteroatoms selected from oxygen, sulphur and nitrogen, the phenyl or heterocyclic ring being optionally substituted by one or two substituents each independently selected from halo, cyano, hydroxycarbonyl, aminocarbonyl, $C_{1-6}$alkylthio, hydroxy, —$NR^{18}R^{19}$, $C_{1-6}$alkylsulphonylamino, $C_{1-6}$alkyl, halo$C_{1-6}$alkyl, $C_{1-6}$alkyloxy or phenyl; or two $R^1$ and $R^2$ substituents adjacent to one another on the phenyl ring may independently form together a bivalent radical of formula —O—CH$_2$—O— (a-1)

—O—CH$_2$—CH$_2$—O— (a-2)

—O—CH=CH— (a-3)

—O—CH$_2$—CH$_2$—   (a-4) or

—O—CH$_2$—CH$_2$—CH$_2$—   (a-5)

$R^{16}$ and $R^{17}$ are independently hydrogen or C$_{1-6}$ alkyl;

$R^{18}$ and $R^{19}$ are independently hydrogen, C$_{1-6}$ alkyl or —(CR$^{16}$R$^{17}$)$_p$—C$_{3-10}$cycloalkyl, or together with the adjacent nitrogen atom form a 5- or 6-membered heterocyclic ring optionally containing one, two or three further heteroatoms selected from oxygen, nitrogen or sulphur and optionally substituted by one or two substituents each independently selected from halo, hydroxy, cyano, nitro, C$_{1-6}$alkyl, haloC$_{1-6}$alkyl, C$_{1-6}$alkyloxy, OCF$_3$, hydroxycarbonyl, C$_{1-6}$alkyloxycarbonyl, aminocarbonyl, mono- or di-(C$_{1-6}$alkyl)aminocarbonyl, amino, mono- or di(C$_{1-6}$alkyl)amino, C$_{1-6}$alkylsulfonylamino, oxime, or phenyl;

$R^{20}$ and $R^{21}$ are independently hydrogen, C$_{1-6}$alkyl, —(CR$^{16}$R$^{17}$)p-C$_{3-10}$cycloalkyl or arylC$_{1-6}$alkyl;

$R^{22}$, $R^{23}$ and $R^{24}$ are independently hydrogen and C$_{1-6}$alkyl or C(O)C$_{1-6}$alkyl;

p is 0 or 1;

$R^3$ is hydrogen, halo, cyano, C$_{1-6}$alkyl, —(CR$^{16}$R$^{17}$)$_p$—C$_{3-10}$cycloalkyl, haloC$_{1-6}$alkyl, cyanoC$_{1-6}$alkyl, hydroxyC$_{1-6}$alkyl, C$_{1-6}$alkyloxyC$_{1-6}$alkyl, arylC$_{1-6}$alkyloxy C$_{1-6}$alkyl, C$_{1-6}$alkylthioC$_{1-6}$alkyl, hydroxycarbonylC$_{1-6}$alkyl, C$_{1-6}$alkylcarbonyl C$_{1-6}$alkyl, C$_{1-6}$alkyloxycarbonylC$_{1-6}$alkyl, —C$_{1-6}$alkyl-NR$^{18}$R$^{19}$, —C$_{1-6}$alkyl-CONR$^{18}$R$^{19}$, arylC$_{1-6}$alkyl, Het$^1$C$_{1-6}$alkyl, C$_{2-6}$alkenyl, —C$_{2-6}$alkenyl NR$^{18}$R$^{19}$, C$_{2-6}$alkynyl, hydroxycarbonyl, C$_{1-6}$alkyloxycarbonyl, aryl, or Het$^1$; or a radical of formula —O—R$^7$   (b-1)

—S—R$^7$   (b-2)

—NR$^8$R$^9$   (b-3) or

—N=CR$^7$R$^8$   (b-4)

wherein R$^7$ is hydrogen, C$_{1-6}$alkyl, —(CR$^{16}$R$^{17}$)$_p$—C$_{3-10}$ cycloalkyl, arylC$_{1-6}$alkyl, C$_{2-6}$alkenyl, C$_{2-6}$alkynyl, C$_{1-6}$alkylcarbonyl or —C$_{1-6}$alkylC(O)OC$_{1-6}$alkyl NR$^{18}$R$^{19}$, or a radical of formula -Alk-OR$^{10}$ or -Alk-NR$^{11}$R$^{12}$;

$R^8$ is hydrogen, C$_{1-6}$alkyl, —(CR$^{16}$R$^{17}$)$_p$—C$_{3-10}$cycloalkyl, C$_{2-6}$alkenyl or C$_{2-6}$alkynyl;

$R^9$ is hydrogen, hydroxy, C$_{1-6}$alkyl, —(CR$^{16}$R$^{17}$)$_p$qj—C$_{3-10}$ cycloalkyl, C$_{1-6}$alkylcarbonylC$_{1-6}$alkyl, arylC$_{1-6}$ alkyl, C$_{2-6}$alkenyl, C$_{2-6}$alkynyl, aryl, C$_{1-6}$alkyloxy, a group of formula —NR$^{18}$R$^{19}$, C$_{1-6}$alkylcarbonylamino, C$_{1-6}$alkylcarbonyl, haloC$_{1-6}$alkylcarbonyl, arylC$_{1-6}$ alkylcarbonyl, arylcarbonyl, C$_{1-6}$alkyloxycarbonyl, trihaloC$_{1-6}$alkyloxycarbonyl, C$_{1-6}$alkyloxyC$_{1-6}$alkylcarbonyl, aminocarbonyl, mono- or di(C$_{1-6}$alkyl) aminocarbonyl wherein the alkyl moiety may optionally be substituted by one or more substituents independently selected from aryl and C$_{1-6}$alkyloxycarbonyl substituents; aminocarbonylcarbonyl, mono- or di(C$_{1-6}$ alkyl)aminoC$_{1-6}$alkylcarbonyl, or a radical of formula -Alk-OR$^{10}$ or Alk-NR$^{11}$R$^{12}$;

wherein Alk is C$_{1-6}$alkanediyl;

$R^{10}$ is hydrogen, C$_{1-6}$alkyl, —(CR$^{16}$R$^{17}$)$_p$—C$_{3-10}$cycloalkyl, C$_{2-6}$alkenyl, C$_{2-6}$alkynyl, C$_{1-6}$alkylcarbonyl or hydroxyC$_{1-6}$alkyl;

$R^{11}$ is hydrogen, C$_{1-6}$alkyl, —(CR$^{16}$R$^{17}$)$_p$—C$_{3-10}$cycloalkyl, C$_{2-6}$alkenyl or C$_{2-6}$alkynyl;

$R^{12}$ is hydrogen, C$_{1-6}$alkyl, —(CR$^{16}$R$^{17}$)$_p$—C$_{3-10}$cycloalkyl, C$_{2-6}$alkenyl, C$_{2-6}$alkynyl or C$_{1-6}$alkylcarbonyl;

$R^4$ is a radical of formula

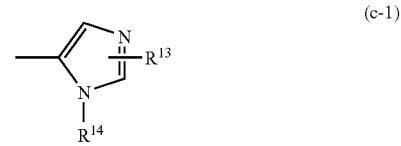   (c-1)

wherein R$^{13}$ is hydrogen, halo or C$_{1-6}$alkyl;

$R^{14}$ is hydrogen or C$_{1-6}$alkyl;

$R^5$ is cyano, hydroxy, halo, C$_{1-6}$alkyl, —(CR$^{16}$R$^{17}$)$_p$—C$_{3-10}$ cycloalkyl, C$_{2-6}$alkenyl, C$_{2-6}$alkynyl, C$_{1-6}$alkyloxy, hydroxycarbonyl, C$_{1-6}$alkyloxycarbonyl, or a group of formula —NR$^{18}$R$^{19}$ or —CONR$^{18}$R$^{19}$;

$R^6$ is hydrogen, C$_{1-6}$alkyl, —(CR$^{16}$R$^{17}$)$_p$—C$_{3-10}$cycloalkyl, cyanoC$_{1-6}$alkyl, —C$_{1-6}$alkylCO$_2$R$^{20}$, aminocarbonylC$_{1-6}$alkyl, —C$_{1-6}$alkyl-NR$^{18}$R$^{19}$, R$^{20}$SO$_2$, R$^{20}$SO$_2$C$_{1-6}$alkyl, —C$_{1-6}$alkyl-OR$^{20}$, —C$_{1-6}$alkyl-SR$^{20}$, —C$_{1-6}$alkylCONR$^{18}$—C$_{1-6}$alkyl-NR$^{18}$R$^{19}$, —C$_{1-6}$ alkylCONR$^{18}$—C$_{1-6}$alkyl-Het$^1$, —C$_{1-6}$alkylCONR$^{18}$—C$_{1-6}$alkyl-Ar$^1$, —C$_{1-6}$alkylCONR$^{18}$-Het$^1$, —C$_{1-6}$alkylCONR$^{18}$Ar$^1$, —C$_{1-6}$alkylCONR$^{18}$—O—C$_{1-6}$alkyl, —C$_{1-6}$alkylCONR$^{18}$—C$_{1-6}$alkenyl, -Alk-Ar$^1$ or -AlkHet$^1$;

Ar$^1$ is phenyl, naphthyl or phenyl or naphthyl substituted by one to five substituents each independently selected from halo, hydroxy, cyano, nitro, C$_{1-6}$alkyl, haloC$_{1-6}$ alkyl, -alkylNR$^{18}$R$^{19}$, C$_{1-6}$alkyloxy, OCF$_3$, hydroxycarbonyl, C$_{1-6}$alkyloxycarbonyl, —CONR$^{18}$R$^{19}$, —NR$^{18}$R$^{19}$, C$_{1-6}$alkylsulfonylamino, oxime, phenyl, or a bivalent substituent of formula —O—CH$_2$—O— or

—O—CH$_2$—CH$_2$—O—;

Het$^1$ is a mono- or bi-cyclic heterocyclic ring containing one or more heteroatoms selected from oxygen, sulphur and nitrogen and optionally substituted by one or two substituents each independently selected from halo, hydroxy, cyano, nitro, C$_{1-6}$alkyl, haloC$_{1-6}$alkyl, -alkylNR$^{18}$R$^{19}$, C$_{1-6}$alkyloxy, OCF$_3$, hydroxycarbonyl, C$_{1-6}$alkyloxycarbonyl, —CONR$^{18}$R$^{19}$, —NR$^{18}$R$^{19}$, C$_{1-6}$alkylsulfonylamino, oxime or phenyl.

2. A compound according to claim 1 wherein r is 1, s is 1 and t is 0; R$^1$ is halo; R$^2$ is halo, C$_{1-6}$alkyl, C$_{1-6}$alkyloxy or C$_{1-6}$alkyloxycarbonyl; R$^3$ is hydrogen or a radical of formula (b-1) or (b-3) wherein R$^7$ is hydrogen or C$_{1-6}$alkyl, R$^8$ is hydrogen and R$^9$ is hydrogen; R$^4$ is a radical of formula (c-1) wherein R$^{13}$ is hydrogen, R$^{14}$ is C$_{1-6}$alkyl; and R$^6$ is hydrogen, C$_{1-6}$alkyl, —(CH$_2$)$_p$—C$_{3-10}$cycloalkyl, —C$_{1-6}$alkylCO$_2$C$_{1-6}$alkyl or -Alk-Ar$^1$.

3. A compound according to claim 1 wherein r is 1, s is 1 and t is 0; R$^1$ is halo; R$^2$ is halo, C$_{1-6}$alkyl or C$_{1-6}$alkyloxy; R$^3$ is hydrogen, hydroxy or amino; R$^4$ is a radical of formula (c-1) wherein R$^{13}$ is hydrogen and R$^{14}$ is C$_{1-6}$alkyl; and R$^6$ is hydrogen or C$_{1-6}$alkyl.

4. A compound according to claim 1 selected from the following compounds:

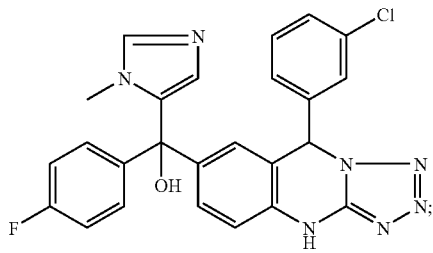

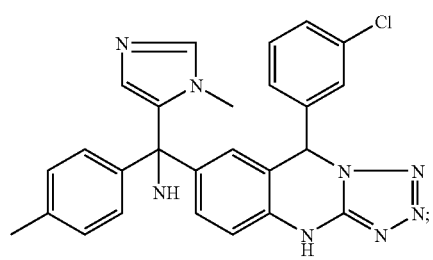

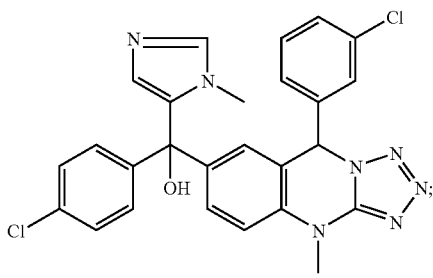

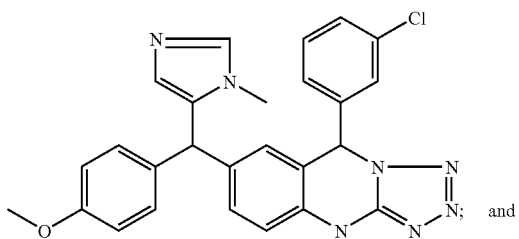

and

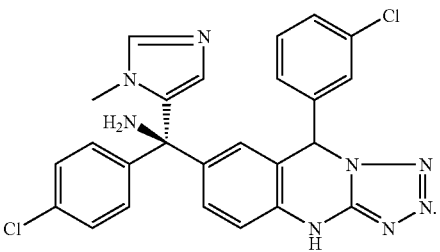

5. A pharmaceutical composition comprising pharmaceutically acceptable carriers and as an active ingredient a therapeutically effective amount of a compound as claimed in claim 1.

6. A process of preparing a pharmaceutical composition as claimed in claim 5 wherein the pharmaceutically acceptable carriers and the compound are intimately mixed.

7. A process for the preparation of a compound as claimed in claim 1 which comprises:
   a) converting intermediates of formula (V) in compounds of formula (I) wherein $R^6$ is hydrogen said compounds being referred to as compounds of formula (I-g) by heating at 120° C. in an appropriate solvent; and

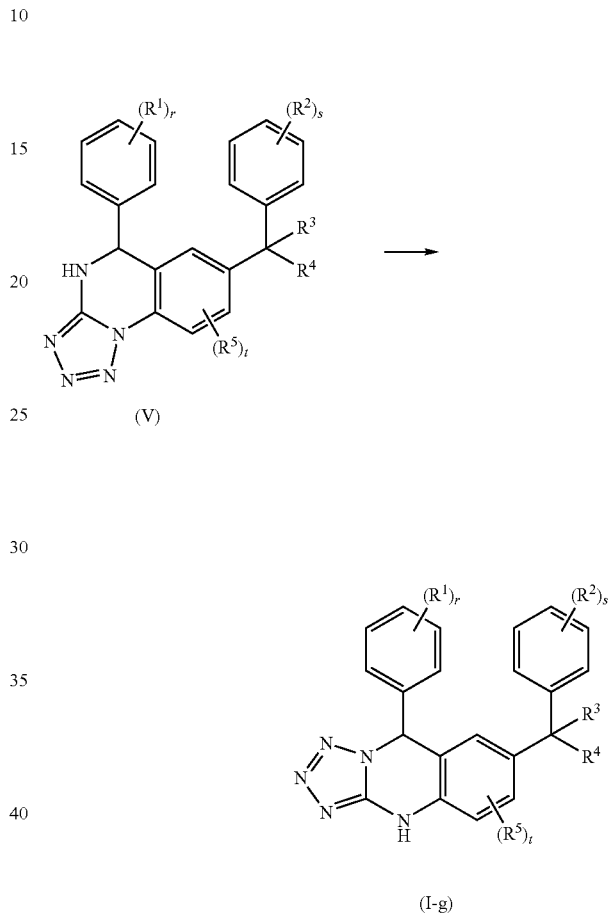

b) reacting an intermediate ketone of formula (II) with an intermediate imidazole of formula (III-a-1) wherein $R^{14}$ is $C_{1-6}$alkyl with the formation of compounds of formula (I) wherein $R^4$ represents a radical of formula (c-1), $R^3$ is hydroxy and $R^{14}$ is $C_{1-6}$alkyl, said compounds being referred to as compounds of formula (I-a-1); and

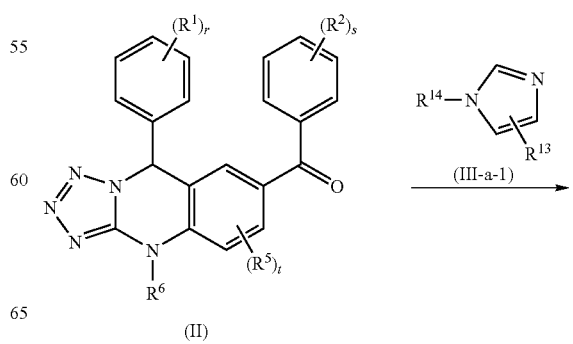

-continued

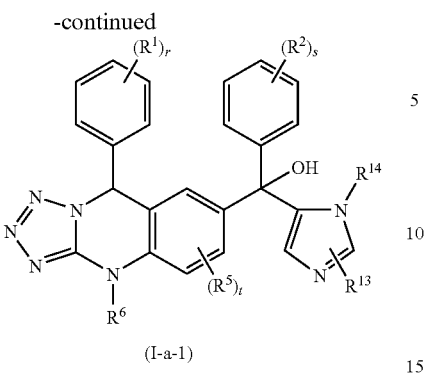
(I-a-1)

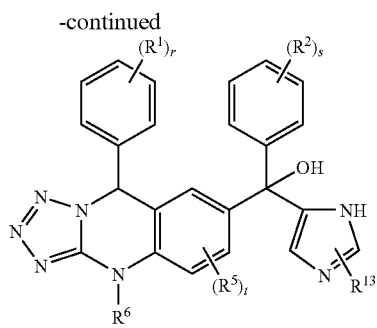
(I-b-1)

c) reacting an intermediate ketone of formula (II) with an intermediate imidazole reagent of formula (III-b-1) wherein P is an optional protective group and R$^{14}$ is hydrogen and subsequently removal of P with the formation of a compound of formula (I) wherein R$^4$ is a radical of formula (c-1), is hydroxy and R$^{14}$ is hydrogen said compound being referred to as compounds of formula (I-b-1); and

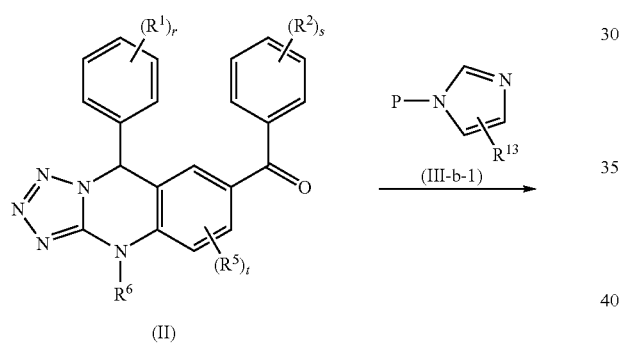

; and d) optionally effecting one or more of the following conversions in any desired order;

(i) converting a compound of formula (I) into a different compound of formula (I);

(ii) converting a compound of formula (I) into a pharmaceutically acceptable salt or N-oxide thereof;

(iii) converting a pharmaceutically acceptable salt or N-oxide of a compound of formula (I) into the parent compound of formula (I);

(iv) preparing a stereochemical isomeric form of a compound of formula (I) or a pharmaceutically acceptable salt or N-oxide thereof.

* * * * *